US010845356B2

(12) United States Patent
Christensen et al.

(10) Patent No.: US 10,845,356 B2
(45) Date of Patent: Nov. 24, 2020

(54) DETERMINATION OF TOTAL BASE NUMBER IN LUBRICANTS

(71) Applicant: ExxonMobil Research and Engineering Company, Annandale, NJ (US)

(72) Inventors: Gary Christensen, Wenonah, NJ (US); Nabila Brabez, Logan Township, NJ (US); Willie A. Givens, Jr., Williamstown, NJ (US); Kevin L. Crouthamel, Hume, VA (US); Andrew D. Satterfield, Hockessin, DE (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 182 days.

(21) Appl. No.: 16/212,117

(22) Filed: Dec. 6, 2018

(65) Prior Publication Data

US 2019/0187119 A1 Jun. 20, 2019

Related U.S. Application Data

(60) Provisional application No. 62/599,160, filed on Dec. 15, 2017.

(51) Int. Cl.
*G01N 33/28* (2006.01)
*C10M 175/00* (2006.01)
*C10N 10/04* (2006.01)
*C10N 30/00* (2006.01)
*C10N 40/25* (2006.01)
(Continued)

(52) U.S. Cl.
CPC ..... *G01N 33/287* (2013.01); *C10M 175/0091* (2013.01); *G01N 33/2876* (2013.01); *G01N 33/2888* (2013.01); *C10N 2010/04* (2013.01); *C10N 2030/52* (2020.05);
(Continued)

(58) Field of Classification Search
CPC ....... F01M 2011/1493; G01N 33/2876; G01N 33/2888; G01N 33/287
See application file for complete search history.

(56) References Cited

U.S. PATENT DOCUMENTS 3,193,356 A * 7/1965 Smith .................. G01N 31/221
  436/101
3,510,260 A * 5/1970 Tovrog ............... G01N 33/2876
  436/60

(Continued)

OTHER PUBLICATIONS

Roman et al., "In-service monitoring of 2-stroke low speed engines with automatic on-line cylinder lubricant analyzer—a key added value for users in 2-stroke engine management", CIMAC Congress, Helsinki, 2016 Paper #54.

(Continued)

*Primary Examiner* — David A. Rogers
(74) *Attorney, Agent, or Firm* — Anthony G. Boone

(57) ABSTRACT

Systems and methods are provided for estimating the total base number of used oil in an engine. The systems and methods can involve characterizing the sulfur content and at least one other element content of the oil both before introduction into the engine and after passing through an engine cylinder during combustion. Depending on the aspect, a total base number of the oil prior to use can also be measured, or the total base number before use can be estimated based on the at least one element content.

24 Claims, 18 Drawing Sheets

(51) Int. Cl.
*C10N 70/00* (2006.01)
*F01M 11/10* (2006.01)

(52) U.S. Cl.
CPC .... *C10N 2040/252* (2020.05); *C10N 2070/00* (2013.01); *F01M 2011/1493* (2013.01)

(56) References Cited

U.S. PATENT DOCUMENTS

| | | | | |
|---|---|---|---|---|
| 3,653,838 | A * | 4/1972 | Glass | G01N 33/2876 436/61 |
| 4,269,604 | A * | 5/1981 | Snowden, Jr. | G01N 33/2888 436/163 |
| 4,741,204 | A * | 5/1988 | Luck | G01N 33/2876 436/61 |
| 4,780,224 | A * | 10/1988 | Jao | C07G 17/008 508/401 |
| 5,067,455 | A * | 11/1991 | Okajima | F01M 9/02 123/196 M |
| 5,366,898 | A * | 11/1994 | Hagstrom | G01N 33/2876 422/537 |
| 5,537,336 | A * | 7/1996 | Joyce | G01N 33/2858 250/301 |
| 5,569,842 | A * | 10/1996 | Silvestri | G01N 33/2888 356/303 |
| 5,800,782 | A * | 9/1998 | Hagstrom | G01N 31/16 422/537 |
| 5,987,976 | A * | 11/1999 | Sarangapani | F01M 11/10 340/438 |
| 6,920,779 | B2 * | 7/2005 | Carlstrom | G01N 33/2876 340/457.4 |
| 7,299,682 | B2 * | 11/2007 | Boyle | G01N 33/2876 324/693 |
| 7,442,936 | B2 * | 10/2008 | Reischman | G01N 21/552 250/339.12 |
| 7,741,122 | B2 | 6/2010 | Reischman | |
| 8,977,421 | B2 * | 3/2015 | Dvorak | G01N 33/2888 701/29.5 |
| 9,354,221 | B2 * | 5/2016 | O'Donnell | G01N 33/2888 |
| 9,714,931 | B2 * | 7/2017 | Prabhu | G01N 33/30 |
| 2002/0125899 | A1 * | 9/2002 | Lvovich | G01N 27/026 324/698 |
| 2003/0164451 | A1 * | 9/2003 | Reischman | G01N 21/3577 250/339.12 |
| 2004/0144355 | A1 * | 7/2004 | Carey | C10M 159/24 123/196 R |
| 2007/0084271 | A1 * | 4/2007 | Boyle | G01N 33/2876 73/53.05 |
| 2007/0196925 | A1 * | 8/2007 | Reischman | G01N 33/287 436/60 |
| 2007/0228281 | A1 * | 10/2007 | Reischman | G01N 21/3577 250/343 |

OTHER PUBLICATIONS

Fogh et al., "On-Board Diagnostic: The new onboard tool for Main Engine condition monitoring with special focus on Cylinder Condition", CIMAC Congress, Helsinki, 2016 Paper #87.
Bots, "Safe and Cost-effective Operation of Slow Speed 2-Stroke Diesel Engines with Scrape Down Oil Analysis (SDA)", CIMAC Congress, Helsinki, 2016 Paper #291.
Vanhelden, "A physio-chemical model of corrosive wear in low-speed diesel engines", CIMAC Congress, Warsaw, 1987 Paper D9.
Robinson, "SEA-Mate Analyser and Blender", Bunker Summit, Greece, 2007.
"Onboard Oil Condition Monitoring", Maritime Journal, Jun. 1, 2006, MJInformation No. 21988.
"D2896: Base Number of Petroleum Products by Potentiometric Perchloric Acid Titration", ASTM International, Feb. 2016.
"D6443: Determination of Calcium, Chlorine, Copper, Magnesium, Phosphorus, Sulfur, and Zinc in Unused Lubricating Oils and Additives by Wavelength Dispersive X-ray Fluorescence Spectrometry", ASTM International, Jan. 2015.

* cited by examiner

DETERMINATION OF TOTAL BASE NUMBER IN LUBRICANTS

CROSS-REFERENCE TO RELATED APPLICATIONS

This application claims priority to U.S. Provisional Application Ser. No. 62/599,160 filed Dec. 15, 2017, which is herein incorporated by reference in its entirety.

FIELD

The disclosure relates to characterization of lubricants to determine a total base number for a used lubricant.

BACKGROUND

Many conventional marine fuels correspond to fuels having a substantial sulfur content. During combustion to operate a diesel engine, the sulfur can be oxidized to form sulfuric acid. This can lead to undesirable corrosion of surfaces and/or seals within the engine if the sulfuric acid can condense on a surface. In order to mitigate this problem, bases such as calcium carbonate can be added to the lubricants used for a marine engine. The fuel and lubricants can interact in the combustion cylinder, so if sufficient base is added to the lubricant, the sulfuric acid formed during combustion of the fuel can be neutralized if it condenses.

One way of determining the total base number of scrape-down oil is by performing on-board characterization of the scrape-down oil. Unfortunately, direct determination of total base number via methods that can be used on a marine vessel is a time-intensive and messy process. It would be preferable to have a method that allowed for determination of total base number without requiring performance of a direct measurement of total base number on a used oil sample.

An alternative method for characterizing whether sufficient base has been added to a lubricant is based on the total base number of the scrape-down oil that remains after combustion. U.S. Pat. No. 7,741,122 describes a method for estimating the total base number of marine scrape-down oil by determining the sulfur content of the scrape-down oil using X-ray fluorescence. Optionally, calcium in the scrape-down oil can also be determined, with the measured value being used to normalize the sulfur values between samples. Although the method allows for an estimate of total base number, further improvements in determining a base number would be desirable.

SUMMARY

In various aspects, a method for determining a total base number for a used lubricating oil, such as a scrape down oil, is provided. The method includes determining (such as measuring) a first sulfur content for a marine lubricating oil prior to introduction into a cylinder in an engine. A first element content for an element in the marine lubricating oil can also be determined prior to introduction into the cylinder in the engine. A second sulfur content and a second element content for oil that has passed through the cylinder during fuel combustion can be measured. Based on the determined and measured values, a total base number can be calculated for the oil that has passed through the cylinder during fuel combustion. Optionally, the calculation of the total base number can be further based on a total base number for the marine lubricating oil prior to introduction into the cylinder.

In some aspects, the first element content can correspond to a content of Ca, Mg, or a combination thereof. In other aspects, the first element content can correspond to a metal content. In still other aspects, the first element content can correspond to a content for an element different from carbon, hydrogen, and sulfur, or an element different from carbon, hydrogen, sulfur, nitrogen, and oxygen.

In some aspects, the method can further include estimating a total base number for the marine lubricating oil prior to introduction into the cylinder based on either the first element content or a third element content (i.e., an element or elements different from the element for the first element content). This estimated total base number for the marine lubricating oil prior to introduction into the cylinder can then be used for the calculation of the total base number for the oil that has passed through the cylinder during fuel combustion. Optionally, the estimated total base number for the marine lubricating base oil prior to introduction into the cylinder can be estimated based on a first polynomial relationship with the first element content or the third element content. The first polynomial relationship can, for example, have a functional form corresponding to $TBN_{fresh}=A*X_{fresh}+B$, where $TBN_{fresh}$ is the total base number for the marine lubricating oil prior to introduction into the cylinder, $X_{fresh}$ is the first element content or third element content, and A and B are constants.

In some aspects, the first element content and/or the third element content can correspond to a combined element content of a plurality of elements, such as a combined metal content of a plurality of metals.

In some aspects, the total base number for the oil that has passed through the cylinder during fuel combustion can be calculated based on a second polynomial relationship between the total base number for the oil that has passed through the cylinder during fuel combustion and the first sulfur content, the second sulfur content, the first element content, and the second element content. The second polynomial relationship can, for example, have a functional form corresponding to $TBN_{used}=(TBN_{fresh}+\alpha*S_{fresh})*(M_{used}/M_{fresh})-\alpha*S_{used}$ where $TBN_{used}$ is the total base number for the oil that has passed through the cylinder during fuel combustion, $TBN_{fresh}$ is the total base number for the marine lubricating oil prior to introduction into the cylinder, $M_{fresh}$ is the first element content, $M_{used}$ is the second element content, $S_{fresh}$ is the first sulfur content, and $S_{used}$ is the second sulfur content. In the second polynomial relationship, $\alpha$ can be determined based on an amount of a strong base required to neutralize a fixed amount of sulfuric acid, such as an amount of NaOH or KOH.

In some aspects, the first element content and the second element content can be determined using the same analysis method and/or using the same analyzer. In some aspects, the first sulfur content and the second sulfur content can be determined using the same analysis method and/or using the same analyzer.

In some aspects, the method can further include determining that the calculated total base number of the oil that has passed through the cylinder is less than a first threshold value or greater than a second threshold value. The first threshold value and/or the second threshold value can be determined by any convenient method, such as based on a percentage of the total base number of the marine lubricating oil prior to entering the cylinder. In such aspects, a corrective action can be performed, such as increasing or decreasing the rate of marine lubricating oil introduction into the cylinder, and/or modifying the total base number of the marine lubricating oil prior to introduction into the cylinder.

In another aspect, a method for determining a total base number for a used lubricating oil is provided, which comprises: determining a first sulfur content for a lubricating oil prior to introduction into a cylinder in an engine; measuring a second sulfur content for oil that has passed through the cylinder during fuel combustion; determining a first element content for an element in the lubricating oil prior to introduction into the cylinder; measuring a second element content for the element in the oil that has passed through the cylinder during fuel combustion; and calculating a total base number for the oil that has passed through the cylinder during fuel combustion based on the first sulfur content, the second sulfur content, the first element content, and the second element content.

DETAILED DESCRIPTION

Figure 1:
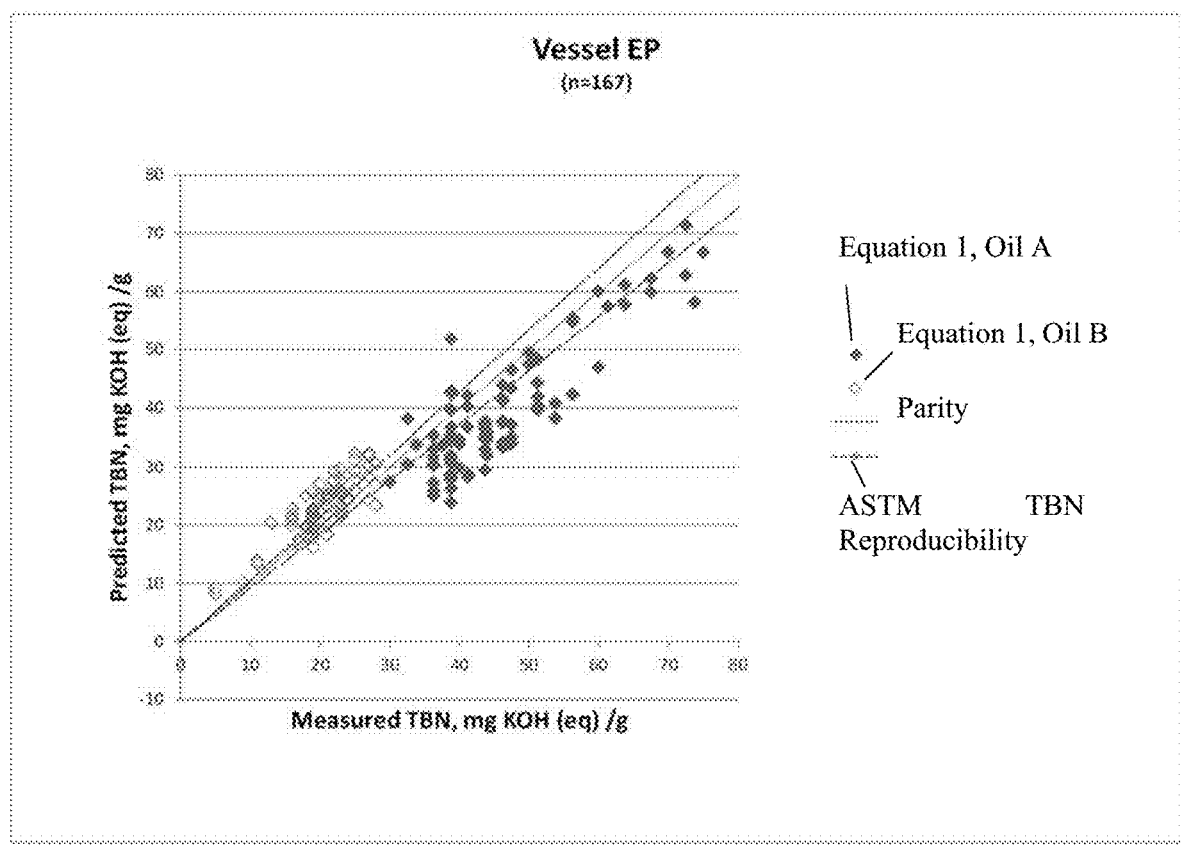
FIG. 1 shows a comparison of measured total base number values for a used lubricant oil with values calculated using a method based on Equation (1) below.

All numerical values within the detailed description and the claims herein are modified by "about" or "approximately" the indicated value, and take into account experimental error and variations that would be expected by a person having ordinary skill in the art. The phrase "major amount" or "major component" as it relates to components included within the lubricating oils of the specification and the claims means greater than or equal to 50 wt. %, or greater than or equal to 60 wt. %, or greater than or equal to 70 wt. %, or greater than or equal to 80 wt. %, or greater than or equal to 90 wt. % based on the total weight of the lubricating oil. The phrase "minor amount" or "minor component" as it relates to components included within the lubricating oils of the specification and the claims means less than 50 wt. %, or less than or equal to 40 wt. %, or less than or equal to 30 wt. %, or greater than or equal to 20 wt. %, or less than or equal to 10 wt. %, or less than or equal to 5 wt. %, or less than or equal to 2 wt. %, or less than or equal to 1 wt. %, based on the total weight of the lubricating oil. The phrase "essentially free" as it relates to components included within the lubricating oils of the specification and the claims means that the particular component is at 0 weight % within the lubricating oil, or alternatively is at impurity type levels within the lubricating oil (less than 100 ppm, or less than 20 ppm, or less than 10 ppm, or less than 1 ppm). The phrase "other lubricating oil additives" as used in the specification and the claims means other lubricating oil additives that are not specifically recited in the particular section of the specification or the claims. For example, other lubricating oil additives may include, but are not limited to, antioxidants, detergents, dispersants, antiwear additives, corrosion inhibitors, viscosity modifiers, metal passivators, pour point depressants, seal compatibility agents, antifoam agents, extreme pressure agents, friction modifiers and combinations thereof.

Diesel engines may generally be classified as slow-speed, medium-speed or high-speed engines, with the slow-speed variety being used for the largest, deep draft marine vessels and in industrial applications. Slow-speed diesel engines are typically direct coupled, direct reversing, two-stroke cycle engines operating in the range of about 57 to 250 rpm and usually run on residual fuels. These engines are of crosshead construction with a diaphragm and stuffing boxes separating the power cylinders from the crankcase to prevent combustion products from entering the crankcase and mixing with the crankcase oil. Medium-speed engines typically operate in the range of 250 to about 1100 rpm and may operate on the 2-stroke or 4-stroke cycle. These engines are trunk piston design, and many operate on residual fuel as well. They may also operate on distillate fuel containing little or no residuals. On deep-sea vessels these engines may be used for propulsion, ancillary applications or both. Slow speed and medium speed marine diesel engines are also extensively used in power plant operations and the methods disclosed herein are also applicable in these applications.

Each type of diesel engine employs lubricating oils to minimize component wear, remove heat, neutralize and disperse combustion products, prevent rust and corrosion and prevent sludge formation or deposits. For some lubricant applications, such as in lubricating cylinders in low-speed, crosshead diesel engines that employ all-loss lubrication systems and combust heavy fuel oil with widely varying sulfur contents, the primary cause of engine wear is in acid induced corrosive wear. Lubricants for these fuels are formulated to have a high total base number (TBN) to neutralize the acids formed by combusting these fuels so as to minimize corrosive wear of these engines. TBN of the used oil is therefore a very important parameter to monitor to ensure adequate protection against corrosive wear.

In various aspects, systems and methods are provided for estimating the total base number of used oil in a marine engine. The systems and methods can involve characterizing the sulfur content and at least one other element content (such as at least one metal content) of the oil both before introduction into the engine and after passing through an engine cylinder during combustion. Depending on the aspect, a total base number of the oil prior to use can also be measured, or the total base number before use can be estimated based on the at least one element content.

Total base number is an indicator of the capacity for a lubricant (or other hydrocarbon fluid) to neutralize additional acid. In other words, total base number is a measure of reserve alkalinity. In this discussion, measured values for total base number are determined according to ASTM D2896. The units of total base number correspond to mg KOH per gram of lubricant.

U.S. Pat. No. 7,741,122 describes a method for estimating the total base number of a used marine lubricating oil, such as a scrape-down oil, based on measuring the sulfur content of the used oil. The method can further include using the sulfur content of the oil prior to use and the total base number of the oil prior to use. The method is described as optionally further characterizing a metal content in the fresh oil, as a method of normalizing the sulfur content in the fresh oil. Although U.S. Pat. No. 7,741,122 describes measuring a metal content in the fresh oil, the method described therein does not contemplate also measuring a metal content in the used oil.

In contrast to the description in U.S. Pat. No. 7,741,122, in various aspects an element content (such as a metal content) for an element can be determined in both fresh lubricating oil and used lubricating oil. By determining an element content in both the fresh oil and the used oil, the element content can be used to account for any change in the oil. In an idealized engine environment, the content of various elements (such as various metals) within the lubricating oil would be relatively constant both before and after passing through an engine cylinder. However, the concentration of elements other than carbon, hydrogen, and sulfur in a lubricating oil can change for a variety of reasons. For example, a marine lubricating oil that includes lighter components may have substantial volatility under the engine operating conditions. Any loss of oil due to vaporization prior to combustion can result in an increase in concentration of metals/other elements in the oil. Similarly, oil can be lost due to combustion of the oil. Such losses can correspond to a loss of hydrocarbon content while not losing other elements so that the element concentration can change due the hydrocarbon loss. In some instances, uncombusted fuel can also be incorporated into the used oil, which could result in a gain in oil (hydrocarbon) volume. Determining both the fresh and used element content of the oil for at least one element can be used to account for such losses (or gains) in oil volume that could lead to a change in concentration of sulfur. Such losses (or gains) in oil volume can also lead to a corresponding change in total base number.

For clarity, it is understood that the at least one element that is characterized in the fresh lubricating oil and the used lubricating oil is an element different from carbon, hydrogen, and sulfur. It is expected that one or more of the factors noted above could lead to a change in carbon and/or hydrogen content between fresh oil and used oil. Since the sulfur content is already being measured, the at least one element can also be different from sulfur. Optionally, the at least one element can be different from carbon, hydrogen, sulfur, nitrogen, and oxygen. Depending on the nature of the fuel being combusted and/or the lubricating oil, nitrogen and/or oxygen could also be present within the hydrocarbon chains in the fuel and/or lubricant, and therefore nitrogen and oxygen are potentially less suitable for use as an element for "normalizing" values between the fresh and used oil.

Any convenient element (or combination of elements) that is not volatile within the lubricating oil environment can be used as an element for characterizing the change in oil volume. One convenient choice can be to use a metal (or other element) that serves as a counter-ion for the base added to the lubricant. Due to the formation of sulfuric acid during combustion of a sulfur-containing fuel, marine lubricants can be "over-based" with a base such as calcium carbonate or magnesium carbonate. Using the counter-ion for the base in the lubricant can be beneficial, as the concentration of this counter-ion can be relatively high, which can reduce the impact of inherent measurement uncertainty. Additionally or alternately, for many lubricating oils the concentration of the counter-ion for the base in fresh oil can have a typical relationship to the total base number of the fresh oil. Thus, measurement of the counter-ion for the base in the fresh oil can be beneficial for determining both the fresh oil total base number and for estimating the oil gain/loss, both of which can be used for calculating a total base number for a used oil. More generally, any metal or other element that is expected to be constant with the amount of lubricant oil injected into the engine (i.e., will not volatilize with light components and/or will not be added as a contaminant with fuel during combustion) can be used as an element for characterizing a change in oil volume.

A used lubricating oil can refer to a lubricating oil after it has passed through an engine cylinder while performing a combustion reaction to operate the engine. A scrape-down oil is an example of a used marine lubricating oil. In various aspects, the total base number for a used lubricating oil can be calculated by determining a sulfur content and at least one metal content for both the fresh oil (before passing through the cylinder) and the used oil.

In some aspects, calculation of a total base number for a used lubricating oil can be further based on a measured value for the total base number of the fresh oil. When a measured value for the total base number of the fresh oil is available, a suitable polynomial expression for calculating the total base number of the used oil can correspond to:

$$TBN_{used} = (TBN_{fresh} + \alpha^* S_{fresh})^* (M_{used}/M_{fresh}) - \alpha^* S_{used} \quad (1)$$

In Equation (1), $TBN_{used}$ is the total base number for the oil that has passed through the cylinder during fuel combustion, $TBN_{fresh}$ is the total base number for the marine lubricating oil prior to introduction into the cylinder, $\alpha$ is a constant, $M_{fresh}$ is metal content of the fresh oil, $M_{used}$ is the corresponding metal content of the used oil, $S_{fresh}$ is the sulfur content of the fresh oil, and $S_{used}$ is the corresponding sulfur content of the used oil. It is noted that the value of $\alpha$ can be related to values for converting acidic sulfur to units related to total base number. For example, in some aspects the value of α can be 35, which is a constant value related to converting from units of sulfur concentration to a total base number having units of mg KOH/g. If total base number were expressed with respect to a different base (such as NaOH), the value of α would correspondingly change.

It is noted that Equation (1) is a relationship that can be applied across various types of lubricating oils and/or across various marine vessels without requiring re-fitting. As shown in the examples below, by measuring sulfur and at least one other element for both fresh oil and used oil, any errors that might occur due to variations in lubricating oil type and/or due to variations between marine vessels can be reduced or minimized.

In other aspects, the total base number for the fresh lubricating oil can be estimated based on a measured element content in the fresh oil. Estimating the total base number of the fresh oil can simplify the process of determining the total base number for the used oil, but with the potential loss of some accuracy in the final determined value. When the total base number of the fresh oil is estimated, a suitable polynomial expression for calculating the total base number of the used oil can correspond to:

$$TBN_{used} = ([A*X_{fresh}+B]+\alpha*S_{fresh})*(M_{used}/M_{fresh}) - \alpha*S_{used} \qquad (2)$$

In Equation (2), $TBN_{used}$ is the total base number for the oil that has passed through the cylinder during fuel combustion, A, B, and α are constants, $M_{fresh}$ is the content of a first element in the fresh oil, $M_{used}$ is the corresponding element content of the used oil, $X_{fresh}$ is the content of the element used for estimating the total base number of the fresh oil, $S_{fresh}$ is the sulfur content of the fresh oil, and $S_{used}$ is the corresponding sulfur content of the used oil. Similar to Equation (1), the relationship in Equation (2) can be used across various lubricating oils and/or across various marine vessels. It is noted that it will often be convenient to have $X_{fresh}$ correspond to the same element as $M_{fresh}$, but $X_{fresh}$ and $M_{fresh}$ can also correspond to different elements.

If the calculated total base number for the used oil is below a first threshold value, the low value can indicate a likelihood of the presence of sulfuric acid within the combustion cylinder environment. This can cause undesirable corrosion of the cylinder walls. Alternatively, if the calculated total base number for the used oil is above a second threshold value, the high value can indicate that too much oil is being delivered to the cylinders and/or that too much base is present in the lubricating oil. Thus, after calculating the total base number for the used oil, the resulting value can be used to perform one or more corrective actions. In some aspects, the corrective action can correspond to adjusting the oil flow rate to the cylinder(s). If the estimated total base number is too low, such as less than a first threshold value (or lower threshold), the flow rate of lubricant to the cylinder(s) can be increased. Although the total base number of the fresh oil is not changed, the higher flow rate means that more base is delivered to the cylinder. Similarly, if the estimated total base number is too high, such as greater than a second threshold (or upper threshold), the flow rate of lubricant to the cylinder(s) can be decreased. This can save on operating costs for the vessel and reduce the volume of waste used oil produced. In some aspects, the first threshold and/or the second threshold for a used base oil can be selected based on the total base number for the corresponding fresh oil. One example of selecting a threshold value based on the total base number for the corresponding fresh oil can be to select a threshold value based on a percentage of the total base number for the corresponding fresh oil (i.e., multiplying the total base number for the fresh oil by a scaling factor). In various aspects, the first threshold value can be 20 mg KOH/g or less, or 15 mg KOH/g or less, or 10 mg KOH/g or less, such as down to roughly 0 mg KOH/g. If the calculated total base number falls below the first threshold value, additional base or detergent (such as $CaCO_3$) can be added to the fresh oil to increase the total base number of the fresh oil by 5 mg KOH/g or more, or 10 mg KOH/g, or 15 mg KOH/g or more, such as up to 25 mg KOH/g or still higher.

Additionally or alternately, calculation of the total base number for a used marine lubricating oil can allow for adjustment of the amount of base and/or detergent added to the fresh oil without requiring collection of a sample of the used oil to perform a measurement of total base number. In some aspects, the amount of base added to the fresh oil, such as $CaCO_3$, can be modified in response to the total base number for the used oil falling below the first threshold value and/or being above the second threshold value. In other aspects, the adjustment of the amount of base can be performed by having an additional on-board tank of engine oil with a higher total base number, so that oil from the additional tank can be added to the fresh oil when the estimated total base number is too low. Still another option can be to select a fresh lubricating oil with a higher (or lower) total base number the next time the vessel is refueled.

It is noted that if a measured value for the total base number of the fresh lubricant is desired, it may be feasible to perform such a measurement at a single point, such as when a lubricant reservoir is filled. The methods described herein can then allow for calculation of total base number of the used lubricant at various convenient times, such as periodically. This can allow for monitoring of the combustion reaction in the engine cylinders to verify that the environment is not becoming too acidic.

Characterization of Sulfur and Additional Elements

The methods described herein can involve determining a content of sulfur for both fresh lubricant oil and used lubricant oil. The content of at least one other element can also be determined for both the fresh lubricant oil and the used lubricant oil.

For the used lubricant oil, determining the sulfur content and the additional element content can preferably correspond to measuring the sulfur content and the additional element content. This can correspond to, for example, measuring the sulfur content and/or element content using equipment present on the marine vessel.

For the fresh lubricant oil, in some aspects at least one of the sulfur content and the additional element content may be provided based on a prior measurement. Thus the determined values for the sulfur content and/or the additional element content of the fresh lubricant oil may correspond to previously determined values. In other aspects, the sulfur content and/or additional element content of the fresh lubricant oil can also be measured on the marine vessel. It can be beneficial to measure the sulfur content and/or the additional element content of the fresh oil using the same measurement technique used for measurements performed on the used oil. Using the same measurement technique is defined herein as using the same type of methodology and/or the same type of device, but a different piece or pieces of equipment. Additionally or alternately, it can be beneficial to measure the sulfur content and/or the additional element content of the fresh oil using the same measurement device or system (i.e., the same equipment) as the used oil.

The sulfur conent of the fresh oil and/or used oil can be measured by any convenient method. The measurement can be as an in-line measurement, or a sample can be withdrawn from a suitable location and a measurement can be performed on the withdrawn sample. One example of a suitable measurement technique can be to use X-ray fluorescence (XRF). For example, sulfur can be measured according to the methodology in ASTM D4294. X-ray fluorescence can also be suitable for measurement of the content of calcium, magnesium, or certain other metals, such as according to the method in ASTM D6443. It is noted that ASTM D6443 is traditionally used for determination of elemental quantities in fresh lubricating oils, but in some aspects it can also be used for determination of an element content in a used lubricating oil, so that the same method is used for determination of element content (and/or optionally sulfur content) in both a fresh lubricant oil and the corresponding used lubricant oil. While XRF and/or the above ASTM methods are suitable for determination of sulfur and other element contents, it is understood that the methods for calculation of total base number described herein can be used with any other convenient measurement techniques for measurement of sulfur and/or metal content.

In some aspects, the total base number of the fresh oil can be determined, such as according to the method in ASTM D2896. In other aspects, the total base number of the fresh oil can be estimated based on the determined value for an additional metal. For example, in many over-based lubricating oil samples, the total base number of the fresh lubricating oil can be related to the calcium content of the fresh lubricating oil. A convenient expression for describing this relationship can be:

$$TBN_{fresh} = A * X_{fresh} + B, \quad (3)$$

In Equation (3), $TBN_{fresh}$ is the total base number for the marine lubricating oil prior to introduction into the cylinder (i.e., fresh oil), $X_{fresh}$ is the determined calcium content (or other element content) in the fresh oil, and A and B are constants.

EXAMPLES

In the following examples, a variety of fresh lubricating oils were used as lubricating oils for engines. Table 1 shows representative measured values for total base number, sulfur content, and calcium content for fresh lubricating oils A-F.

TABLE 1

Characterization of Fresh Lubricating Oils

| Oil | Typical Fresh TBN (mg KOH/g) | Typical Fresh S (wt %) | Typical Fresh Ca (wt %) |
|---|---|---|---|
| A | 100 | 1.1 | 3.8 |
| B | 70 | 1.0 | 2.6 |
| C | 85 | 1.0 | 3.2 |
| D | 60 | 1.0 | 2.2 |
| E | 35 | 0.8 | 1.4 |
| F | 25 | 0.7 | 0.9 |

In the examples that follow, a variety of methods of calculating total base number based on other measured values were used. One method corresponded to using Equation (1). In the version of Equation (1) used in the Examples, a was equal to 35.0. As a variation, in some of the examples, measured values were not available for the fresh oil, so Equation (1) was used in conjuction with the estimates of fresh oil values shown in Table 1. Another method corresponded to using Equation (2). In the version of Equation (2) used in the Examples, A was equal to 26.8 while B was equal to 0. In some alternative aspects not shown in the Examples, A could be set to 25.9 while B could be set to 1.2.

In addition to using Equations (1) and (2), still another method for calculation of total base number corresponds to the method described in U.S. Pat. No. 7,741,122, where total base number is predicted based on the ratio of sulfur to calcium in the scrape-down oil. It is noted that in FIG. 1 of U.S. Pat. No. 7,741,122, a line is shown with a slope of approximately 35. However, as shown below, the methodology in U.S. Pat. No. 7,741,122 produces less accurate predictions for total base number in used oil.

In the following Examples, measured values for the total base number of the used lubricating oils are also provided to allow for a comparison of the accuracy of each of the calculation methods. Where possible, a solid line corresponding to the measured total base number is provided, along with dashed lines showing error bars based on the reproducibility of the method for total base number measurement as provided in ASTM D2896.

Example 1

Figure 2:
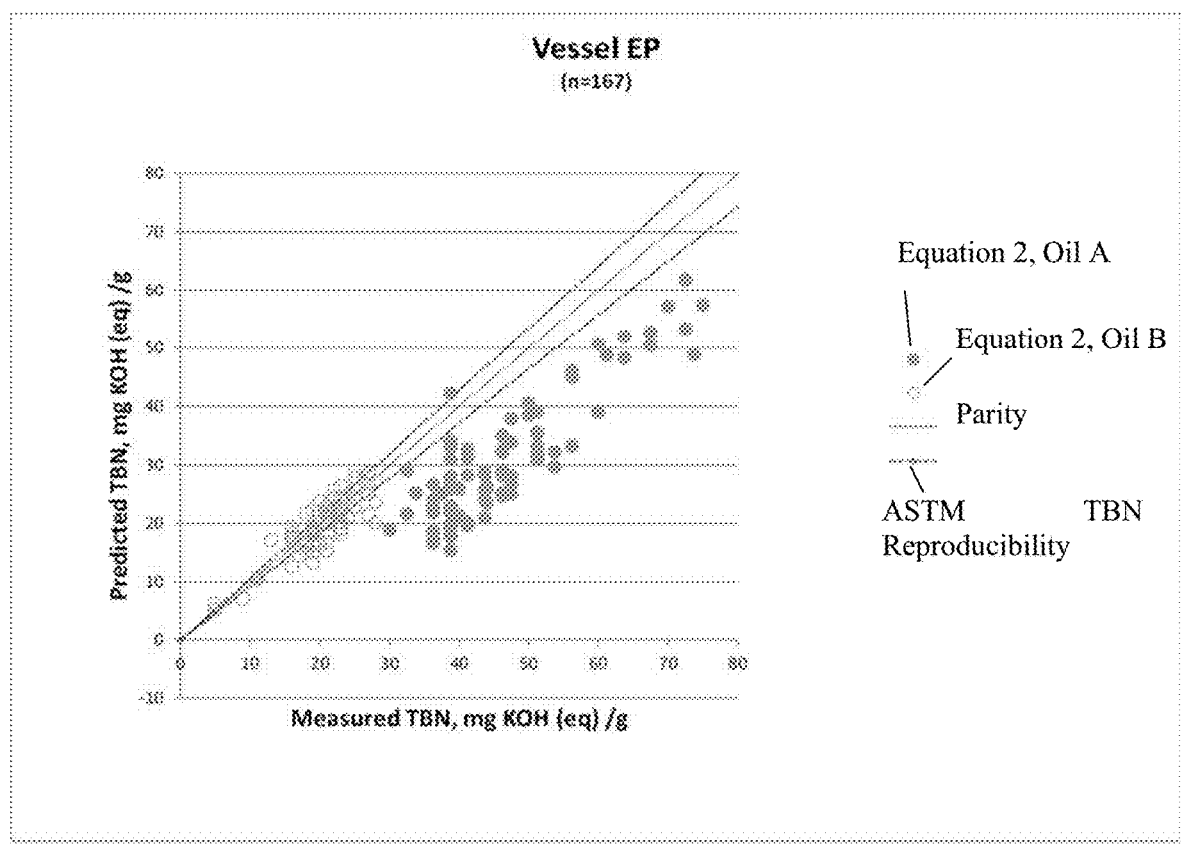
FIG. 2 shows a comparison of measured total base number values for a used lubricant oil with values calculated using a method based on Equation (2) below.
Figure 3:
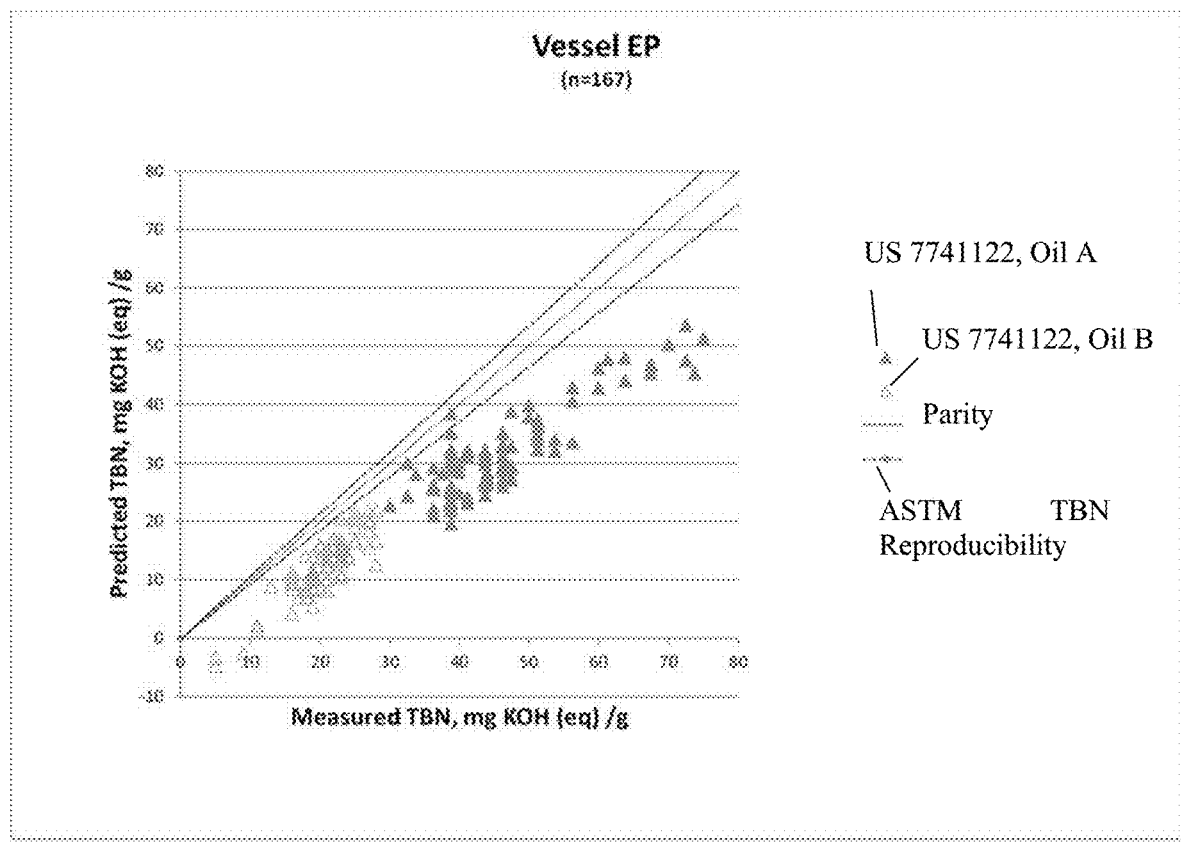
FIG. 3 shows a comparison of measured total base number values for a used lubricant oil with values calculated using a comparative method.

In the first example, oils A and B were run for an extended period in vessel EP; fresh oil and used oil samples had their S, TBN, and Ca measured. It is noted that the typical values shown in Table 1 were not used in this example, since measured fresh values were available. A total of 167 fresh/used oil paired samples were collected and analyzed. FIG. 1 shows a comparison of measured total base number values for the used oil with calculated values based on Equation (1) above. FIG. 2 shows a similar comparison based on Equation (2) above. FIG. 3 shows a similar comparison based on the Equation used in FIG. 4 of U.S. Pat. No. 7,741,122. FIG. 1, FIG. 2, and FIG. 3 also show a parity line, representing the line where the calculated values would equal the measured values. FIG. 1, FIG. 2, and FIG. 3 further show dotted lines corresponding to the reproducibility of the ASTM D2896 method, which was used for measurement of the total base number.

The predicted values shown in FIG. 1 (corresponding to Equation 1) clearly have better agreement with the measurements than the method from U.S. Pat. No. 7,741,122, as shown in FIG. 3. The predicted values in FIG. 2 actually provide the best prediction of total base number for oil B, but also provide the least accurate prediction for oil A. Performance of the three alternative methods for all of the results for both oils is Equation (1)>Equation (2)>U.S. Pat. No. 7,741,122, as seen in the overall Root Mean Square Error (RMSE) in Table 2.

TABLE 2

RMSE for each equation for 167 data points for oil A and B in vessel EP.

Figure 4:
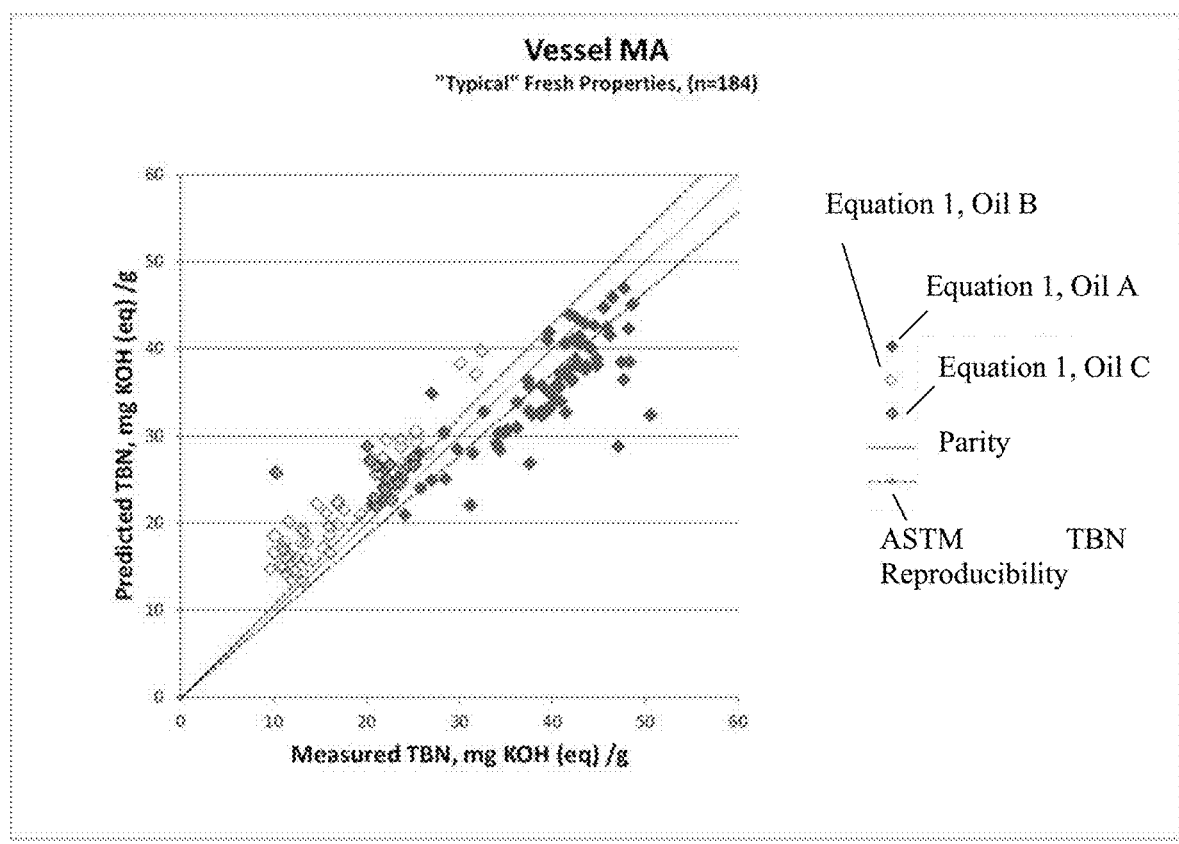
FIG. 4 shows a comparison of measured total base number values for a used lubricant oil with values calculated using a method based on Equation (1) below.

| Equation | Oil A | Oil B | Total |
|---|---|---|---|
| FIG. 4 U.S. Pat. No. 7,741,122 | 15.3 | 8.7 | 12.7 |
| Equation (1) | 8.5 | 3.7 | 6.7 |
| Equation (2) | 16.3 | 2.7 | 12.0 |

There is improvement of both of the new equations over the prediction based on the method from U.S. Pat. No. 7,741,222.

Example 2

Figure 5:
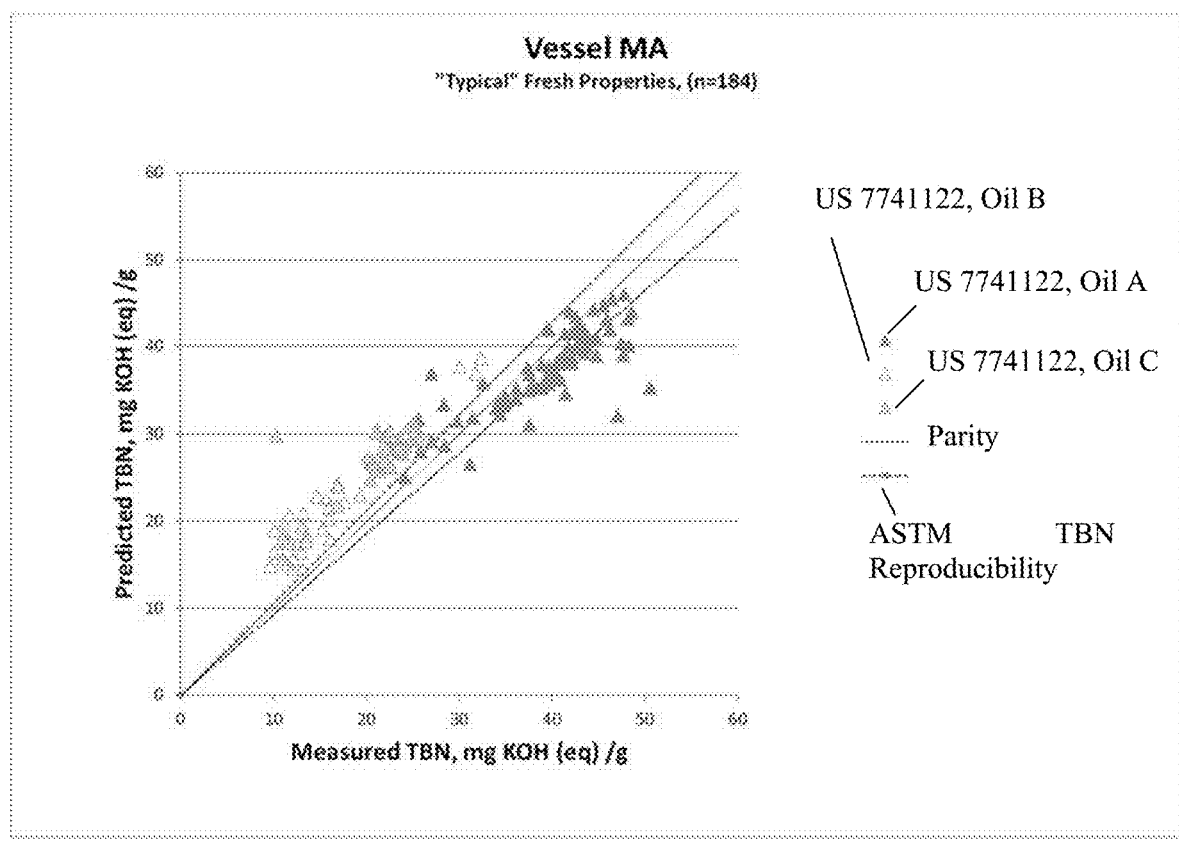
FIG. 5 shows a comparison of measured total base number values for a used lubricant oil with values calculated using a comparative method.

In the second example, oils A, B and C were run for an extended period in vessel MA. Used oil samples had their S, TBN, and Ca measured. A total of 184 used oil samples were collected and analyzed. Fresh oil samples were not available. Therefore, to use Equation (1), the typical properties shown in Table 1 were used for the fresh oil properties. FIG. 4 shows a comparison of the predicted results using Equation (1) with the measured values for total base number of the used oil, while FIG. 5 provides a similar comparison for predictions based on the method used in U.S. Pat. No. 7,741,122. As shown in FIGS. 4 and 5, Equation (1) provides improved accuracy for the calculated total base number of the used oil for oils B and C, while the method used in U.S. Pat. No. 7,741,122 is better for oil A. Overall, in the absence of measured values for the fresh samples in this Example, Equation (1) provided a marginal improvement in prediction accuracy. Table 3 shows the root mean square error for the results in FIGS. 4 and 5.

TABLE 3

RMSE for each equation for 184 data points for oils A, B, and C in vessel MA.

| Equation | Oil A | Oil B | Oil C | All Data |
|---|---|---|---|---|
| FIG. 4 U.S. Pat. No. 7,741,122 | 4.4 | 5.6 | 7.0 | 5.3 |
| Equation (1) | 5.7 | 4.7 | 4.5 | 5.2 |

Example 3

Figure 6:
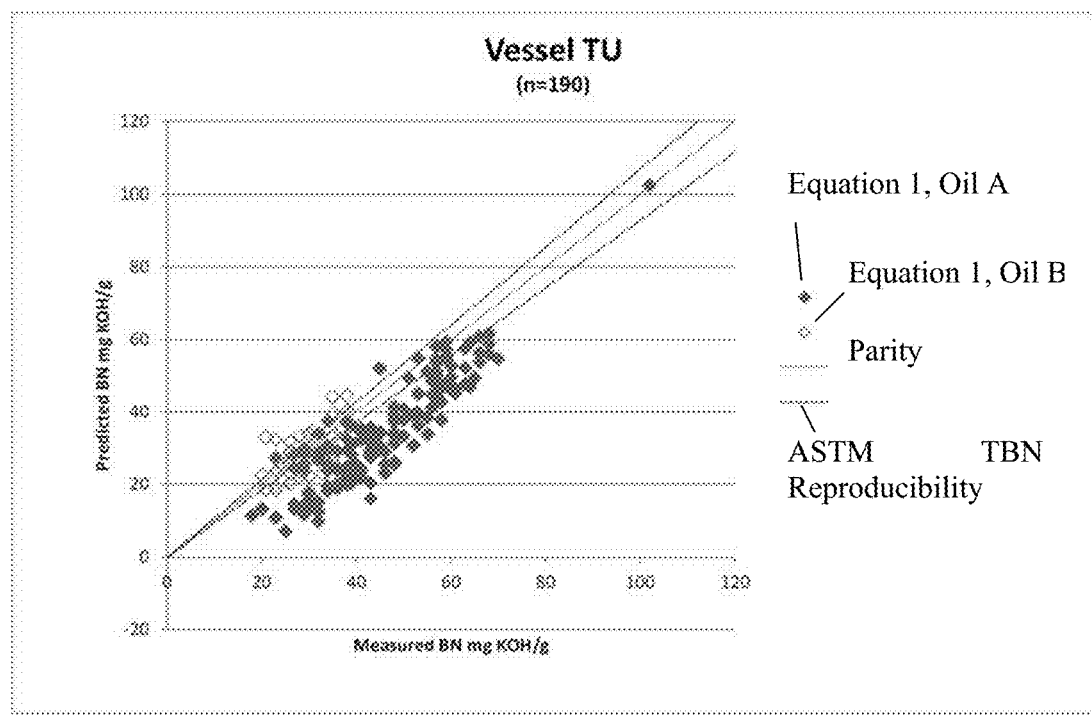
FIG. 6 shows a comparison of measured total base number values for a used lubricant oil with values calculated using a method based on Equation (1) below.
Figure 7:
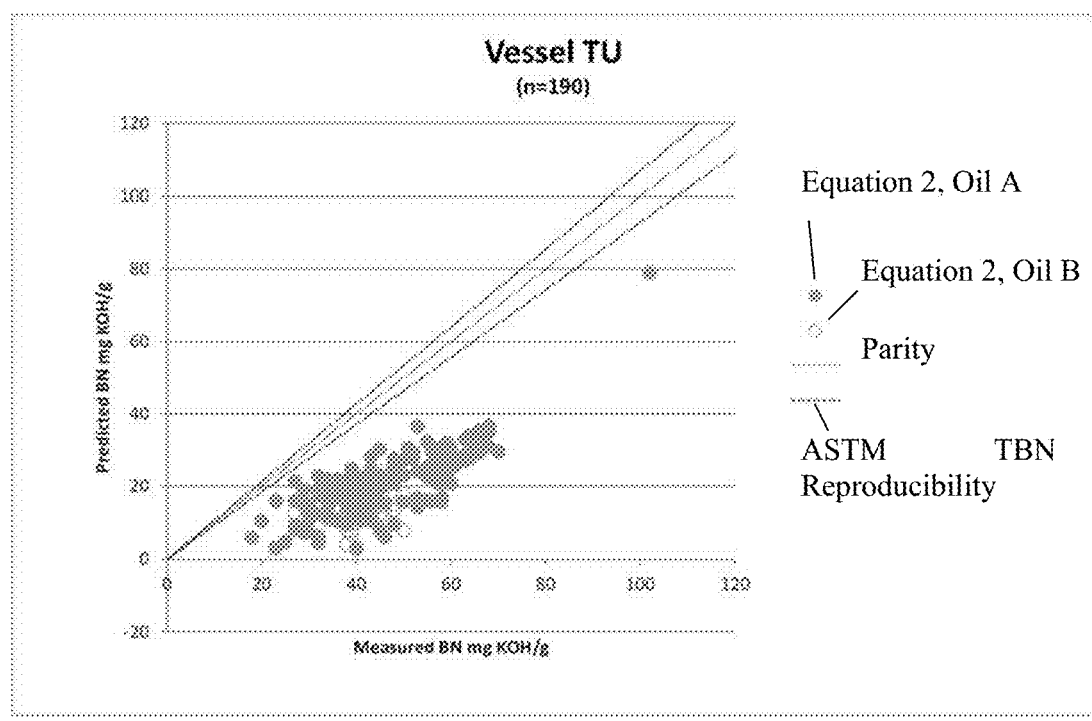
FIG. 7 shows a comparison of measured total base number values for a used lubricant oil with values calculated using a method based on Equation (2) below.
Figure 8:
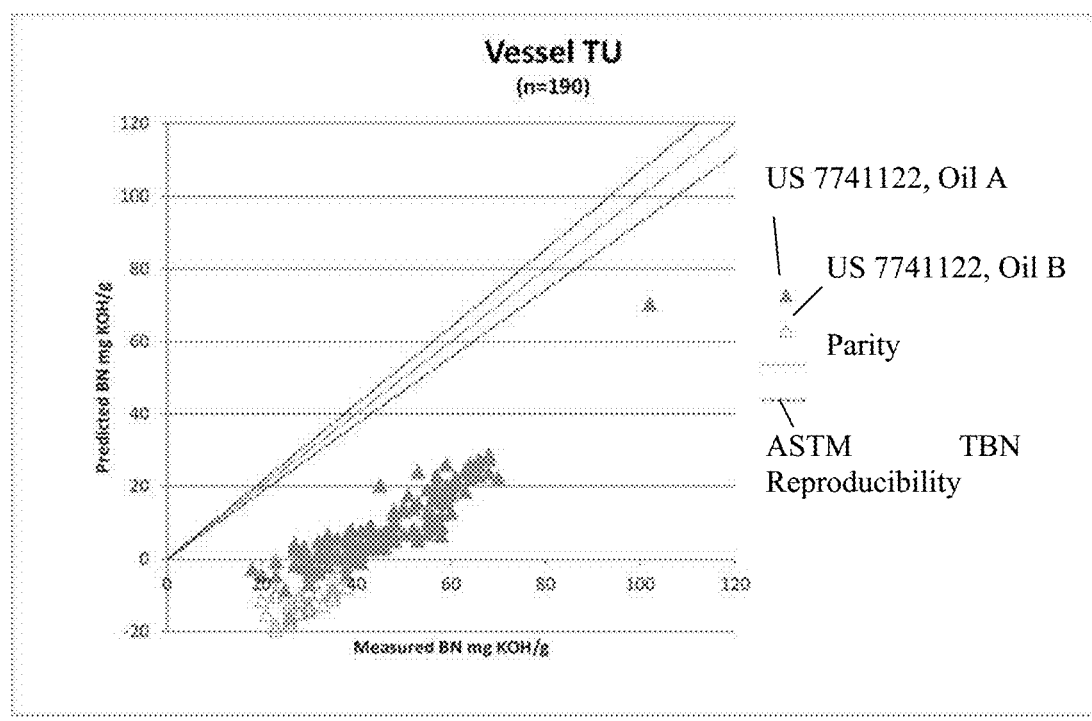
FIG. 8 shows a comparison of measured total base number values for a used lubricant oil with values calculated using a comparative method.

In the third example, oils A and B were run for an extended period in vessel TU; fresh oil and used oil samples had their S, TBN, and Ca measured. A total of 190 fresh/used oil paired samples were collected and analyzed. FIG. 6 shows a comparison of the measured total base number values for the used oils with the calculated values based on Equation (1). FIG. 7 provides a similar comparison for the calculated values based on Equation (2), while FIG. 8 provides a similar comparison for calculated values based on U.S. Pat. No. 7,741,122 (FIG. 4).

As shown in FIG. 6, the calculated total base number values based on Equation (1) provide the best agreement with the total base number values for the used oil. The calculated values based on Equation 2 are better than the values calculated based on U.S. Pat. No. 7,741,122. The Root Mean Square Error (RMSE) for each oil is listed in Table 4.

TABLE 4

RMSE for each equation for 190 data points for oil A and B in vessel TU.

| Equation | Oil A | Oil B |
|---|---|---|
| FIG. 4 U.S. Pat. No. 7,741,122 | 37.3 | 41.1 |
| Equation (1) | 12.6 | 5.7 |
| Equation (2) | 26.1 | 15.3 |

Example 4

Figure 9:
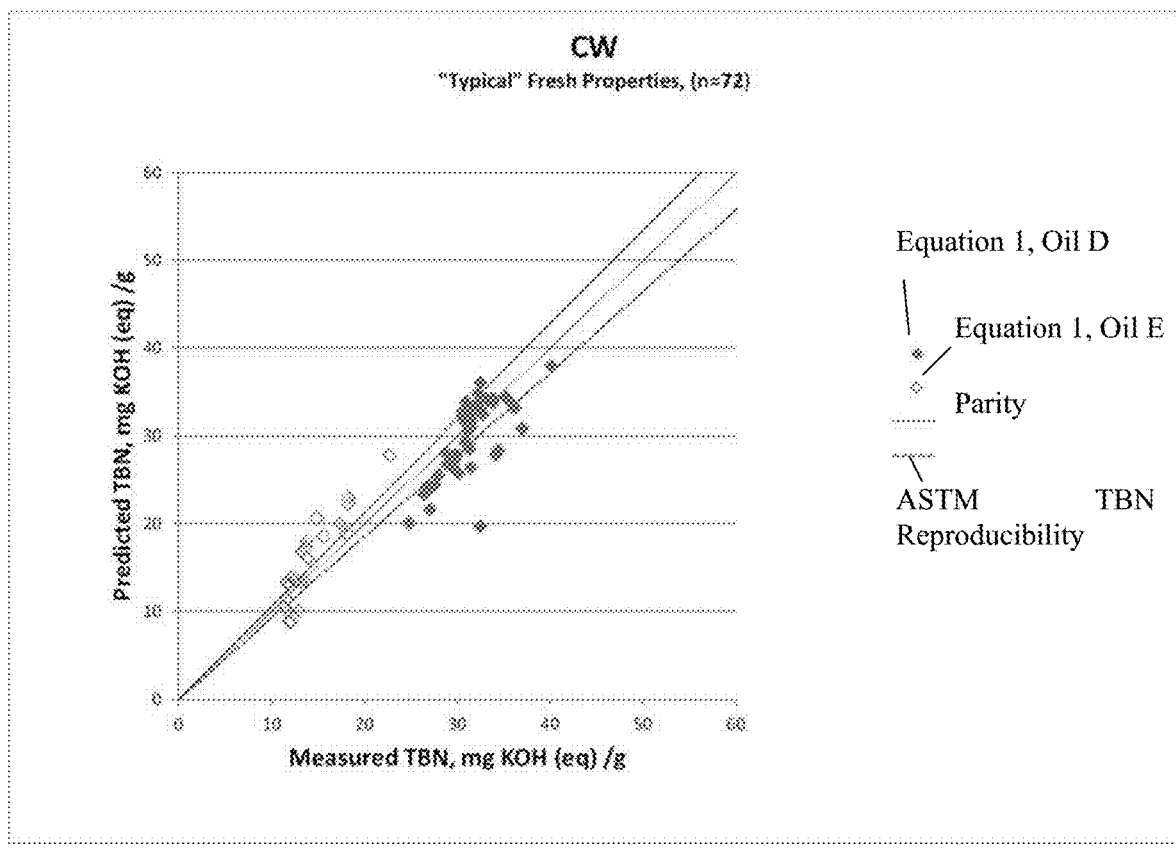
FIG. 9 shows a comparison of measured total base number values for a used lubricant oil with values calculated using a method based on Equation (1) below.
Figure 10:
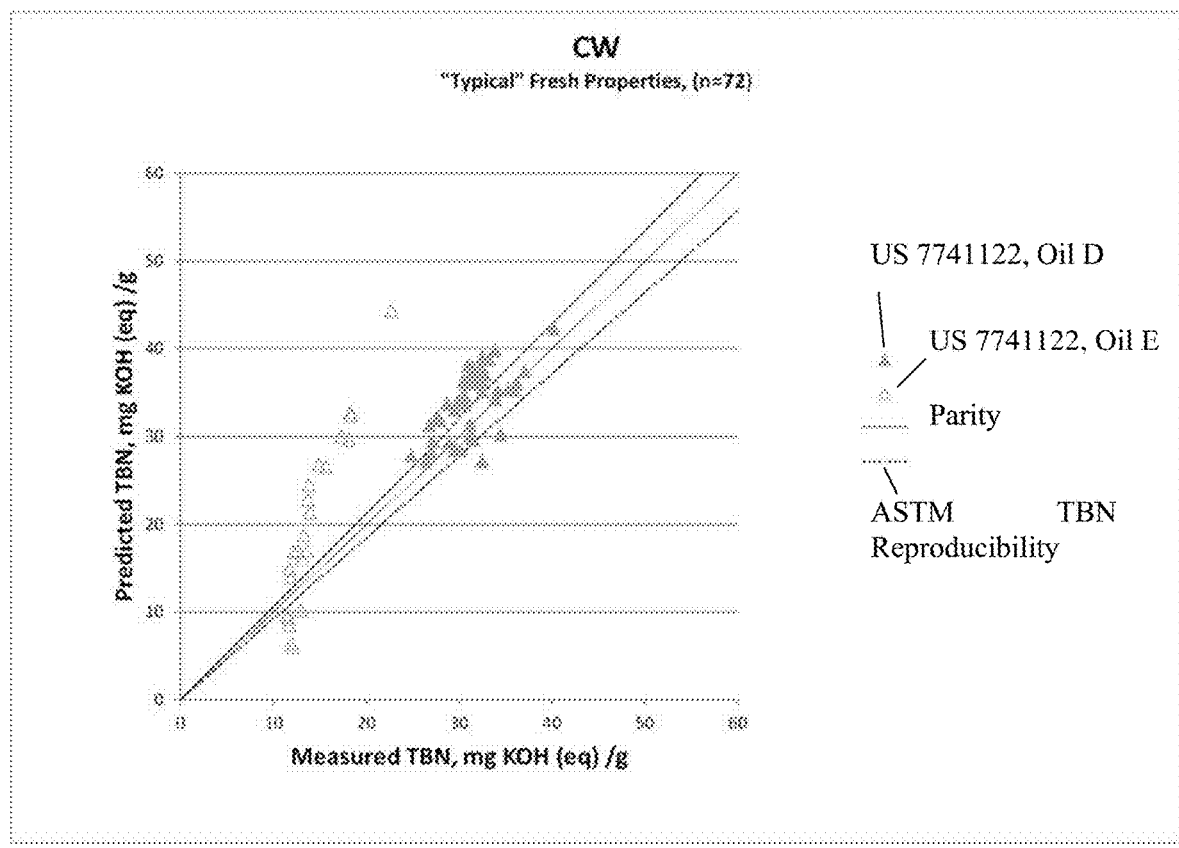
FIG. 10 shows a comparison of measured total base number values for a used lubricant oil with values calculated using a comparative method.

In the fourth example, oils D and E were run for an extended period in vessel CW. Used oil samples had their S, TBN, and Ca measured. A total of 72 used oil samples were collected and analyzed. Fresh oil samples were not available. To use Equation (1), the typical properties shown in Table 1 were used for the fresh oil properties. FIG. 9 shows a comparison of the predicted results using Equation (1) with the measured values for total base number of the used oil, while FIG. 10 provides a similar comparison for predictions based on the method used in U.S. Pat. No. 7,741, 122. As shown in FIG. 9, the predicted total base number values based on Equation (1) provided better accuracy relative to the measured total base number of the used oil, as compared to the values shown in FIG. 10 based on U.S. Pat. No. 7,741,122. Table 5 shows the root mean square error for the results in FIGS. 9 and 10.

TABLE 5

RMSE for each equation for 72 data points for oil D and E in vessel EP.

| Equation | Oil D | Oil E |
|---|---|---|
| FIG. 4 U.S. Pat. No. 7,741,122 | 7.0 | 9.4 |
| Equation (1) | 6.3 | 4.3 |

Example 5

Figure 11:
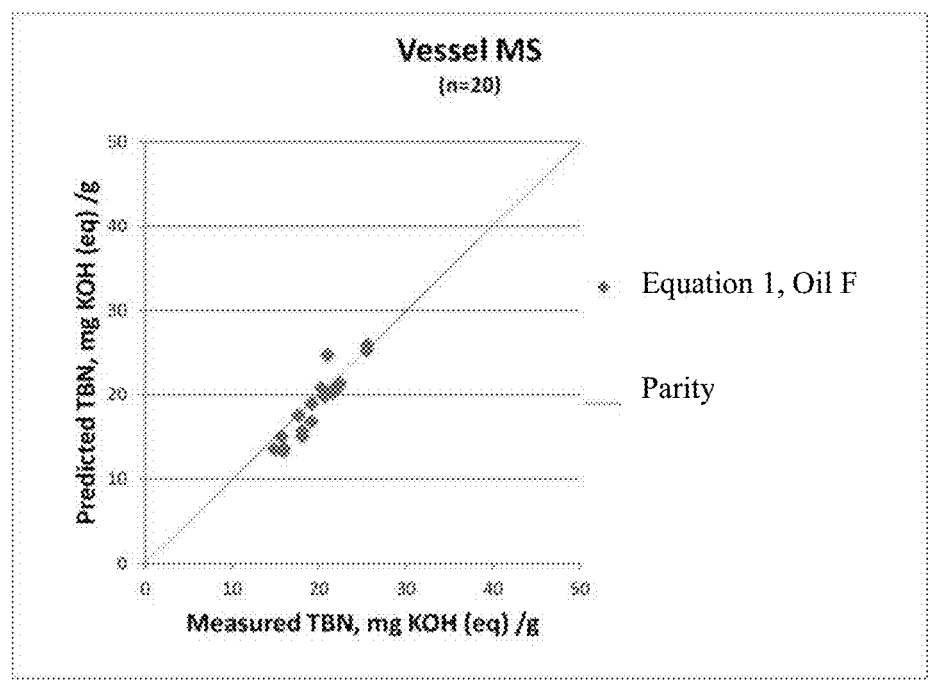
FIG. 11 shows a comparison of measured total base number values for a used lubricant oil with values calculated using a method based on Equation (1) below.
Figure 12:
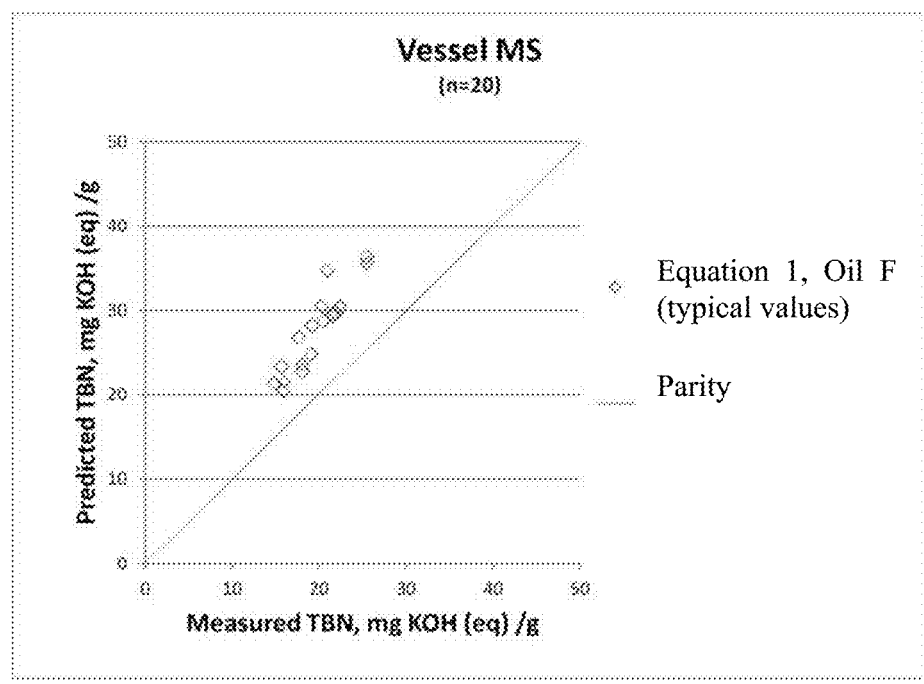
FIG. 12 shows a comparison of measured total base number values for a used lubricant oil with values calculated using a method based on Equation (1) below.
Figure 13:
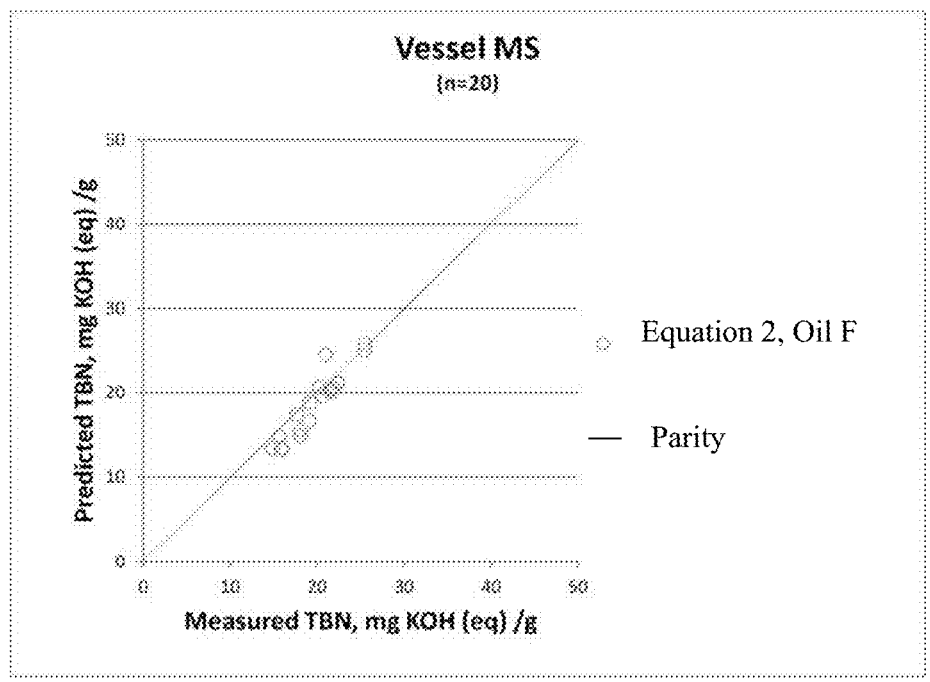
FIG. 13 shows a comparison of measured total base number values for a used lubricant oil with values calculated using a method based on Equation (2) below.
Figure 14:
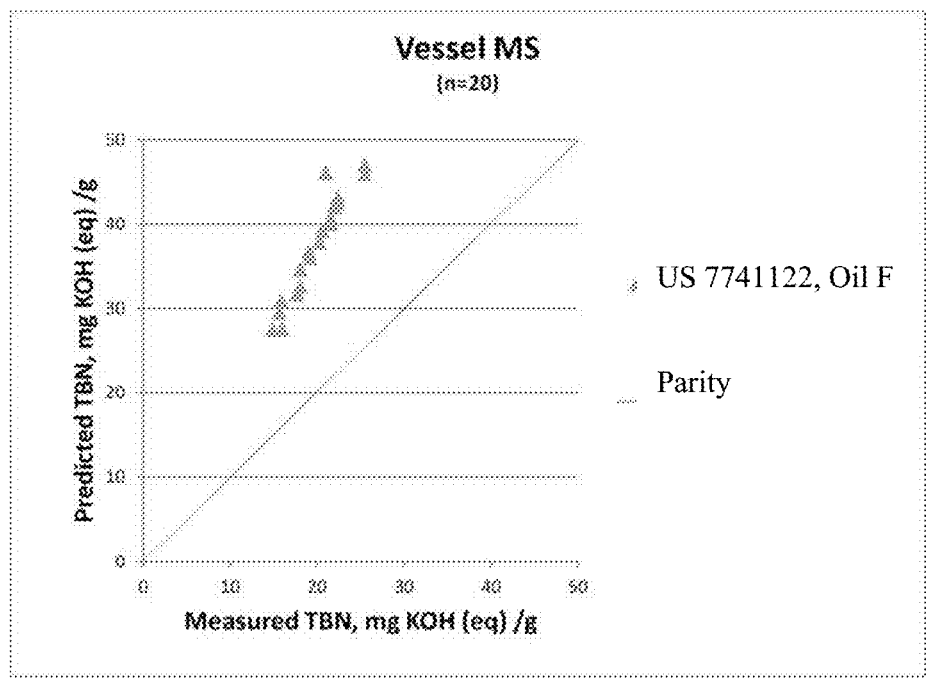
FIG. 14 shows a comparison of measured total base number values for a used lubricant oil with values calculated using a comparative method.

In the fifth example, oil F was run for an extended period in vessel MS; fresh oil and used oil samples had their S, TBN, and Ca measured. A total of 20 fresh/used oil paired samples were collected and analyzed. FIG. 11 shows measured total base number values versus calculated values based on Equation (1). FIG. 12 shows a similar comparison, but instead of using the measured values for the total base number of the fresh oil in Equation (1), the typical values shown in Table 1 were used. FIG. 13 shows a comparison similar to FIG. 11, but with calculated values based on Equation (2). FIG. 14 shows a comparison similar to FIG. 11, but with calculated values based on U.S. Pat. No. 7,741,122.

For this combination of vessel and oil, Equation (1) with actual measured fresh oil properties (FIG. 11) performs almost identically to Equation (2) (FIG. 13). Both are superior to the equation from U.S. Pat. No. 7,741,122 (as shown in FIG. 14). With regard to the difference between FIG. 11 and FIG. 12, using Equation (1) with measured fresh oil properties showed improvement over using Equation (1) with typical fresh oil properties. The data in FIG. 12, however, was still an improvement over the predictions based on U.S. Pat. No. 7,741,122, as shown in FIG. 14. The Root Mean Square Error (RMSE) for each method is shown in Table 6.

TABLE 6

RMSE for each equation for 20 data points for oil F in vessel MS.

| Equation | Oil F |
|---|---|
| U.S. Pat. No. 7,741,122 | 19.5 |
| Equation (1) (Measured Fresh) | 5.0 |
| Equation (1) (Typical Fresh) | 10.6 |
| Equation (2) | 5.0 |

Example 6—Variation in Ca(Used) Versus Ca(Fresh)

Figure 15:
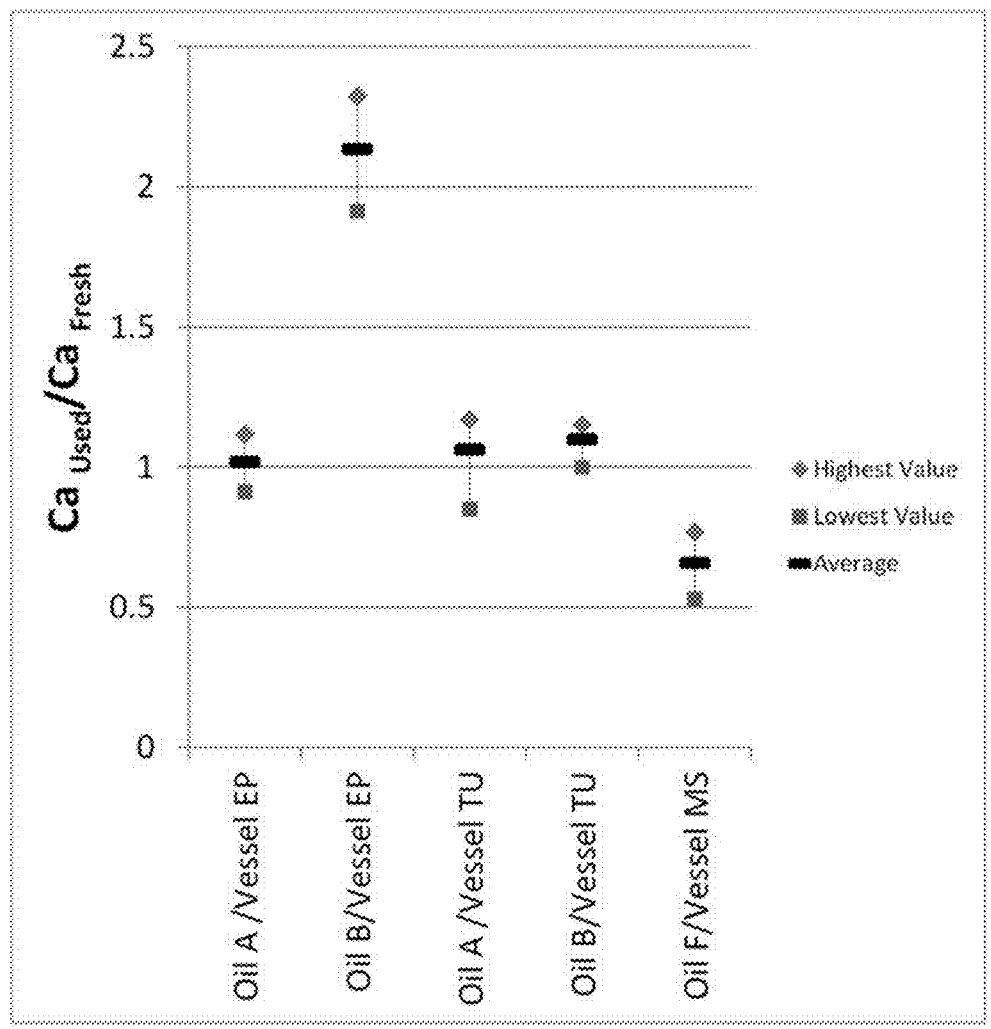
FIG. 15 shows variation in the ratio of calcium content in fresh lubricant oil versus used lubricant oil for various samples.

In Equation (1) and Equation (2) as applied to Examples 1 to 5, the concentration of Ca in the fresh and used oil corresponded to the additional metal. The ratio of $Ca_{used}$ to $Ca_{fresh}$ was found to vary between the different vessels described above as well as between oil samples on the same vessel. FIG. 15 shows the average ratio of $Ca_{used}$ to $Ca_{fresh}$ for several of the combinations of oil samples and vessels described in the Examples above. Additionally, error bars are shown for each of the average ratio values to show the variation in the ratio within individual samples. This variation both between vessels and between samples for a single vessel provides an additional demonstration of why the methods described herein provided superior estimates of total base number for used oil relative to the method used in U.S. Pat. No. 7,741,122. In U.S. Pat. No. 7,741,122, the measured value of Ca in the used oil was used as a normalizing factor for the sulfur content of the used oil, without regard to the Ca content of the fresh oil. Such normalization based on only the Ca content in used oil cannot capture the variation in concentration due to volatility changes. By contrast, FIG. 15 shows that volatility and/or other factors related to loss or gain of lubricant oil amount were significant for many of the oil samples.

Example 7—Triggering Action Resulting from TBN Estimate

As described in the Detailed Description, an estimated used oil TBN either above an upper threshold value, or, below a lower threshold value should produce an action by the vessel operator to change in the amount of base supplied to the cylinder, either by changing the oil feed rate with the same oil, or, changing the TBN of the oil being fed to the cylinder. The two threshold values triggering action could be established by the equipment manufacturer, or, by the equipment operator. For this example, two threshold values based on a percentage of the initial oil TBN have been arbitrarily chosen to illustrate the action required, and are:

Upper Threshold (UT)=45% of Initial Oil TBN

Lower Threshold (LT)=20% of Initial Oil TBN

Using these threshold percentages, the data presented in Examples 1 through 5 were analyzed to determine what fraction of the data points would trigger action, either by being greater than the Upper Threshold (>UT), or, by being less than the Lower Threshold (<LT). These percentages are shown in Tables 7, 8, and 9.

TABLE 7

Percentage of data points triggering action for vessel EP for data in Example 1.

| | Oil A (# = 89) | | Oil B (# = 78) | |
| --- | --- | --- | --- | --- |
| Equation | >UT | <LT | >UT | <LT |
| Measured | 45% | 0% | 0% | 8% |
| FIG. 4 U.S. Pat. No. 7,741,122 | 11% | 1% | 0% | 62% |
| Equation (1) | 21% | 0% | 8% | 6% |
| Equation (2) | 15% | 11% | 0% | 9% |

TABLE 8

Percentage of data points triggering action for vessel MA for data in Example 2.

| | Oil A (# = 81) | | Oil B (# = 72) | | Oil C (# = 31) | |
| --- | --- | --- | --- | --- | --- | --- |
| Equation | >UT | <LT | >UT | <LT | >UT | <LT |
| Measured | 15% | 0% | 6% | 41% | 0% | 4% |
| FIG. 4 U.S. Pat. No. 7,741,122 | 3% | 0% | 7% | 0% | 0% | 0% |
| Equation (1) | 4% | 0% | 7% | 4% | 0% | 0% |

TABLE 9

Percentage of data points triggering action for vessel TU for data in Example 3.

| | Oil A (# = 152) | | Oil B (# = 38) | |
| --- | --- | --- | --- | --- |
| Equation | >UT | <LT | >UT | <LT |
| Measured | 43% | 1% | 32% | 0% |
| FIG. 4 U.S. Pat. No. 7,741,122 | 1% | 85% | 0% | 100% |
| Equation (1) | 28% | 14% | 37% | 0% |
| Equation (2) | 1% | 48% | 0% | 63% |

TABLE 10

Percentage of data points triggering action for vessel CW for data in Example 4.

| | Oil D (# = 48) | | Oil E (# = 24) | |
| --- | --- | --- | --- | --- |
| Equation | >UT | <LT | >UT | <LT |
| Measured | 91% | 0% | 21% | 0% |
| FIG. 4 U.S. Pat. No. 7,741,122 | 100% | 0% | 63% | 8% |
| Equation (1) | 72% | 0% | 46% | 0% |

TABLE 11

Percentage of data points triggering action for vessel MS for data in Example 5.

| | Oil F (# = 20) | |
| --- | --- | --- |
| Equation | >UT | <LT |
| Measured | 60% | 0% |
| FIG. 4 U.S. Pat. No. 7,741,122 | 100% | 0% |
| Equation (1) | 60% | 0% |
| Equation (2) | 60% | 0% |

In the data shown in Tables 7 to 11, the first row of each table corresponds to the percentage of used oil TBN values, based on a measurement according to ASTM D2896, that resulted in a trigger for an actionable event based on either the upper threshold (45% of initial oil TBN) or the lower threshold (20% of initial oil TBN). These trigger percentages based on the measured used oil TBN values can be used as a baseline for evaluating the estimates provided by Equation (1), Equation (2), and the method used in U.S. Pat. No. 7,741,122.

As shown in Tables 7 to 11, the trigger percentages based on the used oil TBN estimates determined according to Equation (1) provided the closest overlap with the trigger percentages based on the measured values. This can be seen from both a qualitative and a quantitative standpoint.

From a qualitative standpoint, this can be evaluated based on the number of instances in Tables 7 to 11 where either a)

the measured values resulted in a non-zero trigger percentage, while an estimating method resulted in a zero trigger percentage, or b) the measured values resulted in a zero trigger percentage, while an estimating method resulted in non-zero trigger percentage. Under this qualitative standard, the used oil estimates determined according to Equation (1) had only two qualitative variations from the measured used oil TBN values. These occurred for the upper threshold for Oil B in Table 7 and the lower threshold for Oil C in Table 8. By contrast, the method from U.S. Pat. No. 7,741,122 resulted in 6 qualitative variations across Tables 7-11.

Quantitatively, Equation (1) also provided trigger percentages with greater similarity to the trigger percentages based on the measured used oil TBN values. From a quantitative standpoint, this can be determined based on the number of instances in Tables 7 to 11 where there is a difference of more than 20% between i) the trigger percentage based on the measured values and ii) the trigger percentage based on an estimated TBN. Under this quantitative standard, the trigger percentages based on estimates provided by Equation (1) again provided the closest match with the trigger percentages based on the measured values. In Tables 7 to 11, the trigger percentages based on the used oil TBN estimate determined according to Equation (1) had only three instances of a quantitative variation in trigger percentages greater than 20% (relative to the trigger percentages based on measured used oil TBN values). These quantitative differences are shown for the upper threshold for Oil A in Table 7, the lower threshold for Oil B in Table 8, and the upper threshold for Oil E in Table 10. By contrast, method from U.S. Pat. No. 7,741,122 resulted in nine quantitative variations. This includes the quantitative variations for Oil A and Oil B in Table 9, where the method from U.S. Pat. No. 7,741,122 resulted in a quantitative variation for both the upper threshold and lower threshold for both oils.

With regard to Equation (2), data was not available for Equation (2) in either Table 8 or Table 10. However, for the instances where a comparison could be made between Equation (2) and the method from U.S. Pat. No. 7,741,122, Equation (2) also performed better from a quantitative viewpoint. In the smaller sample size of Tables 7, 9, and 11, the used oil TBN estimates based on Equation (2) resulted in three qualitative variations and five quantitative variations. By contrast, the method from U.S. Pat. No. 7,741,122 resulted in three qualitative variations and seven quantitative variations. It is noted that the trigger percentage values based on the estimates of used oil TBN from Equation (2) generally had a closer magnitude to the trigger percentages based on the measured values, as compare with the method from U.S. Pat. No. 7,741,122.

Example 8

Figure 16:
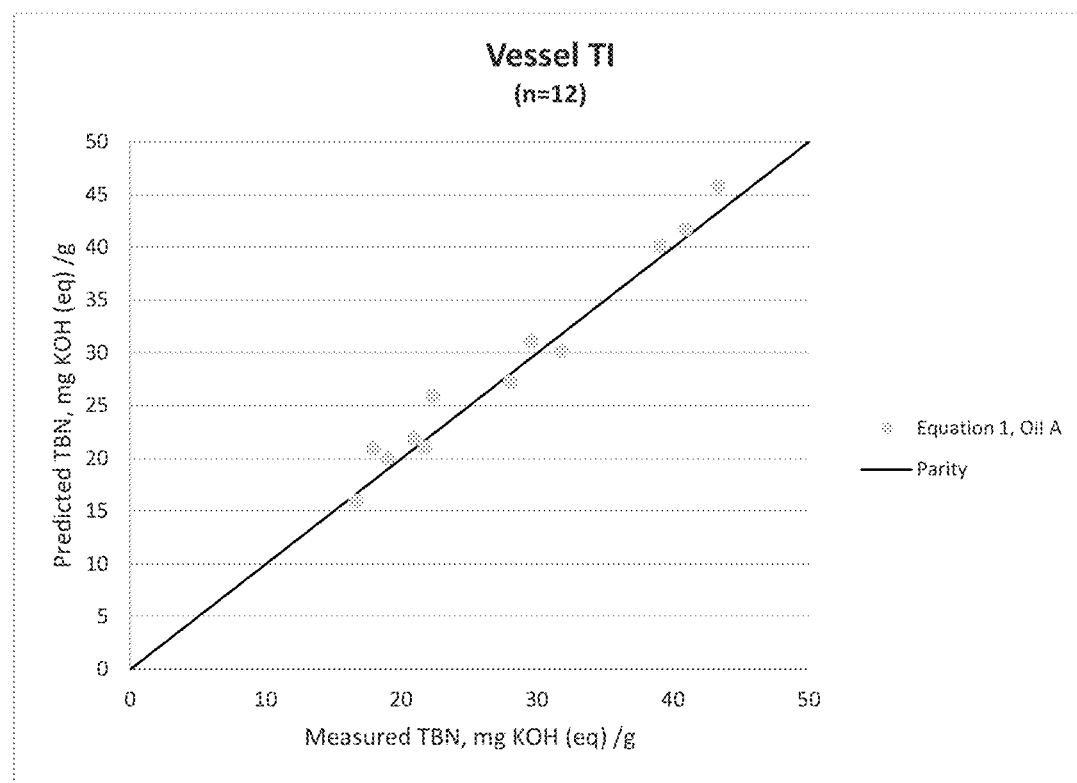
FIG. 16 shows a comparison of measured total base number values for a used lubricant oil with values calculated using equation 1 of the inventive method.
Figure 17:
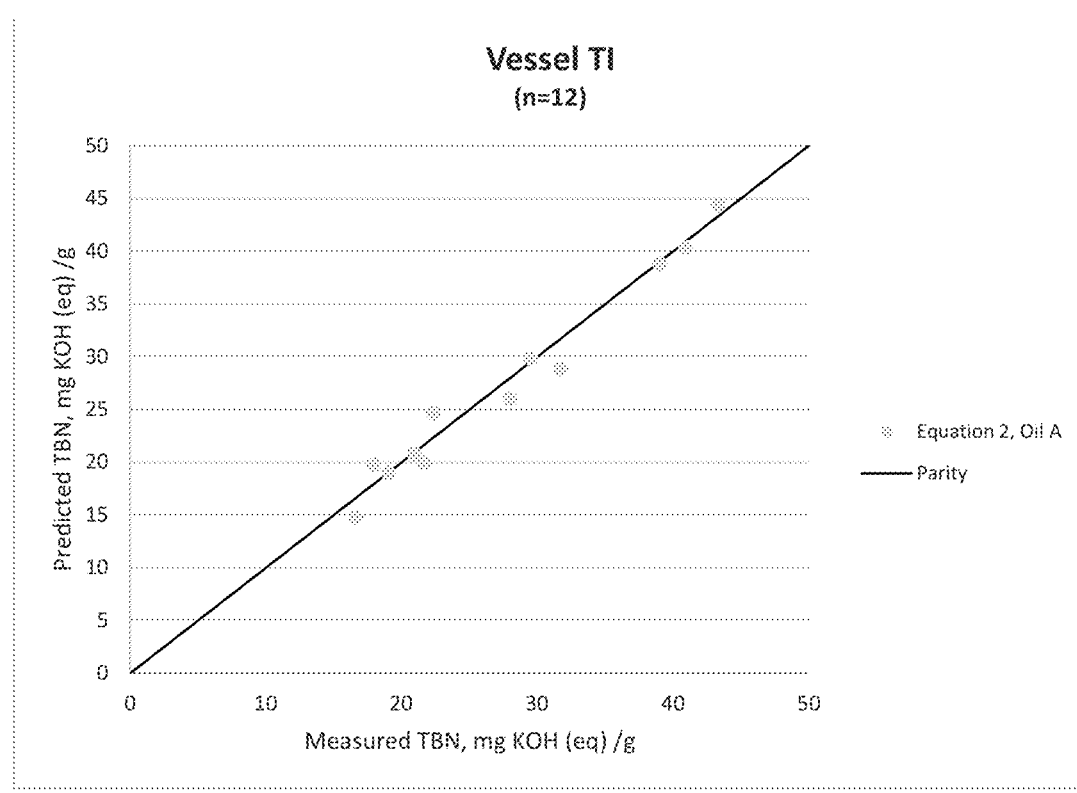
FIG. 17 shows a comparison of measured total base number values for a used lubricant oil with values calculated using equation 2 of the inventive method.
Figure 18:
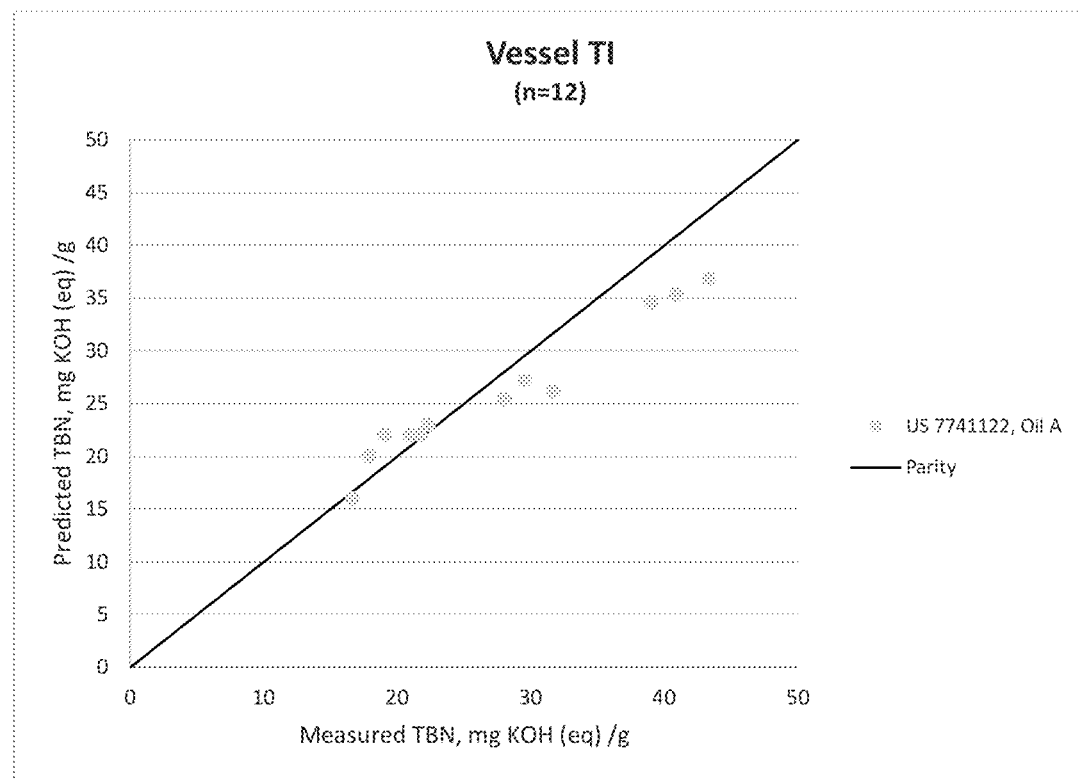
FIG. 18 shows a comparison of measured total base number values for a used lubricant oil with values calculated using a comparative method.

Fresh oil samples were collected at the same time as used oil samples to accurately represent the oil passing through the engine. In this example 8, oil A was run for an extended period in vessel TI; fresh oil and used oil samples had their S and Ca measured onboard the vessel via XRF analysis. The samples were then sent to a lab where TBN was measured via ASTM method D2896 titration. A total of 12 fresh/used oil paired samples were collected and analyzed. FIG. 16 shows measured total base number values versus calculated values based on Equation (1). FIG. 17 shows a comparison similar to FIG. 16, but with calculated values based on Equation (2). FIG. 18 shows a comparison similar to FIG. 16, but with calculated values based on U.S. Pat. No. 7,741,122.

For this combination of vessel and oil, Equation (1) with actual measured fresh oil properties (FIG. 16) performs almost identically to Equation (2) (FIG. 17). Both are superior to the equation from U.S. Pat. No. 7,741,122 (as shown in FIG. 18). The Root Mean Square Error (RMSE) for each method is shown in Table 12.

TABLE 12

RMSE for each equation for 12 data points for oil A in vessel TI.

| Equation | Oil A |
| --- | --- |
| U.S. Pat No. 7,741,122 | 3.5 |
| Equation (1) (Measured Fresh) | 1.6 |
| Equation (2) | 1.8 |

TABLE 13

Percentage of data points triggering action for vessel TI for data in Example 8.

| | Oil A (# = 12) | |
| --- | --- | --- |
| Equation | >UT | <LT |
| Measured | 0% | 25% |
| FIG. 4 U.S. Pat. No. 7,741,122 | 0% | 8% |
| Equation (1) | 0% | 17% |
| Equation (2) | 8% | 8% |

Additional Embodiments

Embodiment 1

A method for determining a total base number for a used lubricating oil, comprising: determining a first sulfur content for a marine lubricating oil prior to introduction into a cylinder in an engine; measuring a second sulfur content for oil that has passed through the cylinder during fuel combustion; determining a first element content for an element in the marine lubricating oil prior to introduction into the cylinder; measuring a second element content for the element in the oil that has passed through the cylinder during fuel combustion; and calculating a total base number for the oil that has passed through the cylinder during fuel combustion based on the first sulfur content, the second sulfur content, the first element content, and the second element content.

Embodiment 2

The method of Embodiment 1, wherein calculating the total base number for the oil that has passed through the cylinder during fuel combustion is further based on a total base number for the marine lubricating oil prior to introduction into the cylinder, the method optionally further comprising measuring the total base number for the marine lubricating oil prior to introduction into the cylinder.

Embodiment 3

The method of any of the above embodiments, wherein determining a first sulfur content for a marine lubricating oil prior to introduction into a cylinder comprises measuring a sulfur content of a sample of the marine lubricating oil.

Embodiment 4

The method of any of the above embodiments, wherein the first element content comprises a content of Ca, Mg, or a combination thereof.

Embodiment 5

The method of any of Embodiments 1-3, wherein the first element content comprises a metal content, or wherein the first element content comprises a content of an element different from carbon, hydrogen, and sulfur, or wherein the first element comprises a content of an element different from carbon, hydrogen, sulfur, nitrogen, and oxygen.

Embodiment 6

The method of any of the above embodiments, further comprising: estimating a total base number for the marine lubricating oil prior to introduction into the cylinder based on the first element content, wherein calculating the total base number for the oil that has passed through the cylinder during fuel combustion is further based on a total base number for the marine lubricating oil prior to introduction into the cylinder.

Embodiment 7

The method of Embodiment 6, wherein estimating the total base number for the marine lubricating oil prior to introduction into the cylinder based on the first element content comprises estimating the total base number for the marine lubricating oil prior to introduction into the cylinder based on a first polynomial relationship with the first element content, the first polynomial relationship optionally comprising a functional form corresponding to $TBN_{fresh} = A*X_{fresh} + B$, where $TBN_{fresh}$ is the total base number for the marine lubricating oil prior to introduction into the cylinder, $X_{fresh}$ is the first element content, and A and B are constants.

Embodiment 8

The method of any of Embodiments 1-5, further comprising: estimating a total base number for the marine lubricating oil prior to introduction into the cylinder based on a third element content of the marine lubricating oil prior to introduction into the cylinder, the third element content corresponding to an element different from the element corresponding to the determined first element content, wherein calculating the total base number for the oil that has passed through the cylinder during fuel combustion is further based on a total base number for the marine lubricating oil prior to introduction into the cylinder.

Embodiment 9

The method of Embodiment 8, wherein estimating the total base number for the marine lubricating oil prior to introduction into the cylinder based on the third element content comprises estimating the total base number for the marine lubricating oil prior to introduction into the cylinder based on a first polynomial relationship with the third element content, the first polynomial relationship optionally comprising a functional form corresponding to $TBN_{fresh} = A*X_{fresh} + B$, where $TBN_{fresh}$ is the total base number for the marine lubricating oil prior to introduction into the cylinder, $X_{fresh}$ is the third element content, and A and B are constants.

Embodiment 10

The method of Embodiment 8 or 9, wherein the third element content comprises a combined element content of a plurality of elements, or wherein the third element content comprises a combined metal content of a plurality of metals.

Embodiment 11

The method of any of the above embodiments, wherein the total base number for the oil that has passed through the cylinder during fuel combustion is calculated based on a second polynomial relationship between the total base number for the oil that has passed through the cylinder during fuel combustion and the first sulfur content, the second sulfur content, the first element content, and the second element content, the second polynomial relationship optionally comprising a functional form corresponding to $TBN_{used} = (TBN_{fresh} + \alpha*S_{fresh})*(M_{used}/M_{fresh}) - \alpha*S_{used}$ where $TBN_{used}$ is the total base number for the oil that has passed through the cylinder during fuel combustion, $TBN_{fresh}$ is the total base number for the marine lubricating oil prior to introduction into the cylinder, $\alpha$ is a constant, $M_{fresh}$ is the first element content, $M_{used}$ is the second element content, $S_{fresh}$ is the first sulfur content, and $S_{used}$ is the second sulfur content, and wherein $\alpha$ is optionally determined based on an amount of a strong base required to neutralize a fixed amount of sulfuric acid.

Embodiment 12

The method of any of the above embodiments, wherein the oil that has passed through the cylinder during fuel combustion comprises a scrape down oil.

Embodiment 13

The method of any of the above embodiments, wherein the first element content and the second element content are determined using the same analysis method, using the same analyzer, or a combination thereof; or wherein the first sulfur content and the second sulfur content are determined using the same analysis method, using the same analyzer, or a combination thereof.

Embodiment 14

The method of any of the above embodiments, a) wherein the method further comprises determining that the calculated total base number of the oil that has passed through the cylinder is less than a first threshold value, and increasing a rate of introducing the marine lubricating oil into the cylinder; b) wherein the method further comprises determining that the calculated total base number of the oil that has passed through the cylinder is greater than a second threshold value, and decreasing a rate of introducing the marine lubricating oil into the cylinder; c) wherein the method further comprises determining that the calculated total base number of the oil that has passed through the cylinder is less than a first threshold value, and modifying an amount of base added to the marine lubricating oil prior to introduction into the cylinder; d) wherein the method further comprises determining that the calculated total base number of the oil that has passed through the cylinder is greater than a second threshold value, and modifying an amount of base added to the marine lubricating oil prior to introduction into the cylinder; or e) a combination of two or more of a), b), c) and d).

Embodiment 15

The method of Embodiment 14, wherein the first threshold value and/or the second threshold value comprises a threshold value that is determined based on the total base number for the marine lubricating oil prior to introduction into the cylinder, the first threshold value and/or the second threshold value optionally being determined based on a percentage of the total base number of the marine lubricating oil prior to introduction into the cylinder.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for determining a total base number for a used lubricating oil, comprising:
   determining a first sulfur content for a marine lubricating oil prior to introduction into a cylinder in an engine;
   measuring a second sulfur content for oil that has passed through the cylinder during fuel combustion;
   determining a first element content for an element in the marine lubricating oil prior to introduction into the cylinder;
   measuring a second element content for the element in the oil that has passed through the cylinder during fuel combustion; and
   calculating a total base number for the oil that has passed through the cylinder during fuel combustion based on the first sulfur content, the second sulfur content, the first element content, and the second element content.

2. The method of claim 1, wherein calculating the total base number for the oil that has passed through the cylinder during fuel combustion is further based on a total base number for the marine lubricating oil prior to introduction into the cylinder.

3. The method of claim 2, the method further comprising measuring the total base number for the marine lubricating oil prior to introduction into the cylinder.

4. The method of claim 1, wherein determining a first sulfur content for a marine lubricating oil prior to introduction into a cylinder comprises measuring a sulfur content of a sample of the marine lubricating oil.

5. The method of claim 1, wherein the first element content comprises a content of Ca, Mg, or a combination thereof.

6. The method of claim 1, wherein the first element content comprises a metal content, or wherein the first element content comprises a content for an element different from carbon, hydrogen, and sulfur, or wherein the first element comprises a content for an element different from carbon, hydrogen, sulfur, nitrogen, and oxygen.

7. The method of claim 1, further comprising:
   estimating a total base number for the marine lubricating oil prior to introduction into the cylinder based on the first element content,
   wherein calculating the total base number for the oil that has passed through the cylinder during fuel combustion is further based on a total base number for the marine lubricating oil prior to introduction into the cylinder.

8. The method of claim 7, wherein estimating the total base number for the marine lubricating oil prior to introduction into the cylinder based on the first element content comprises estimating the total base number for the marine lubricating oil prior to introduction into the cylinder based on a first polynomial relationship with the first element content.

9. The method of claim 8, wherein the first polynomial relationship comprises a functional form corresponding to $$TBN_{fresh} = A \ast X_{fresh} + B,$$

where $TBN_{fresh}$ is the total base number for the marine lubricating oil prior to introduction into the cylinder, $X_{fresh}$ is the first element content, and A and B are constants.

10. The method of claim 1, further comprising:
   estimating a total base number for the marine lubricating oil prior to introduction into the cylinder based on a third element content of the marine lubricating oil prior to introduction into the cylinder, the third element content corresponding to an element different from the element corresponding to the determined first element content,
   wherein calculating the total base number for the oil that has passed through the cylinder during fuel combustion is further based on a total base number for the marine lubricating oil prior to introduction into the cylinder.

11. The method of claim 10, wherein estimating the total base number for the marine lubricating oil prior to introduction into the cylinder based on the third element content comprises estimating the total base number for the marine lubricating oil prior to introduction into the cylinder based on a first polynomial relationship with the third element content, and wherein the first polynomial relationship comprises a functional form corresponding to $$TBN_{fresh} = A \ast X_{fresh} + B,$$

where $TBN_{fresh}$ is the total base number for the marine lubricating oil prior to introduction into the cylinder, $X_{fresh}$ is the third element content, and A and B are constants.

12. The method of claim 10, wherein the third element content comprises a combined element content of a plurality of elements.

13. The method of claim 1, wherein the total base number for the oil that has passed through the cylinder during fuel combustion is calculated based on a second polynomial relationship between the total base number for the oil that has passed through the cylinder during fuel combustion and the first sulfur content, the second sulfur content, the first element content, and the second element content.

14. The method of claim 13, wherein the second polynomial relationship comprises a functional form corresponding to $$TBN_{used} = (TBN_{fresh} + \alpha \ast S_{fresh}) \ast (M_{used}/M_{fresh}) - \alpha \ast S_{used}$$

where $TBN_{used}$ is the total base number for the oil that has passed through the cylinder during fuel combustion, $TBN_{fresh}$ is the total base number for the marine lubricating oil prior to introduction into the cylinder, $\alpha$ is a constant, $M_{fresh}$ is the first element content, $M_{used}$ is the second element content, $S_{fresh}$ is the first sulfur content, and $S_{used}$ is the second sulfur content.

15. The method of claim 14, wherein $\alpha$ is determined based on an amount of a strong base required to neutralize a fixed amount of sulfuric acid.

16. The method of claim 1, wherein the oil that has passed through the cylinder during fuel combustion comprises a scrape down oil.

17. The method of claim 1, wherein the first element content and the second element content are determined using the same analysis method, using the same analyzer, or a combination thereof.

18. The method of claim 1, wherein the first sulfur content and the second sulfur content are determined using the same analysis method, using the same analyzer, or a combination thereof.

19. The method of claim 1, further comprising determining that the calculated total base number of the oil that has passed through the cylinder is less than a first threshold value, and increasing a rate of introducing the marine lubricating oil into the cylinder.

20. The method of claim 19, wherein the first threshold value comprises a threshold value that is determined based on the total base number for the marine lubricating oil prior to introduction into the cylinder.

21. The method of claim 1, further comprising determining that the calculated total base number of the oil that has passed through the cylinder is greater than a second threshold value, and decreasing a rate of introducing the marine lubricating oil into the cylinder.

22. The method of claim 21, wherein the second threshold value comprises a threshold value that is determined based on the total base number for the marine lubricating oil prior to introduction into the cylinder.

23. The method of claim 1, further comprising determining that the calculated total base number of the oil that has passed through the cylinder is a) less than a first threshold value or b) greater than a second threshold value, and modifying an amount of base added to the marine lubricating oil prior to introduction into the cylinder.

24. A method for determining a total base number for a used lubricating oil, comprising:
    determining a first sulfur content for a lubricating oil prior to introduction into a cylinder in an engine;
    measuring a second sulfur content for oil that has passed through the cylinder during fuel combustion;
    determining a first element content for an element in the lubricating oil prior to introduction into the cylinder;
    measuring a second element content for the element in the oil that has passed through the cylinder during fuel combustion; and
    calculating a total base number for the oil that has passed through the cylinder during fuel combustion based on the first sulfur content, the second sulfur content, the first element content, and the second element content.

\* \* \* \* \*